United States Patent
Podoleanu et al.

(10) Patent No.: US 7,466,423 B2
(45) Date of Patent: Dec. 16, 2008

(54) OPTICAL MAPPING APPARATUS

(75) Inventors: Adrian Podoleanu, Canterbury (GB); Adrian Bradu, Canterbury (GB); Chris Dainty, Galway (IE); David Merino, Galway (IE)

(73) Assignees: University of Kent, Kent (GB); National University of Ireland, Galway (IE)

( * ) Notice: Subject to any disclaimer, the term of this patent is extended or adjusted under 35 U.S.C. 154(b) by 172 days.

(21) Appl. No.: 11/239,677

(22) Filed: Sep. 30, 2005

(65) Prior Publication Data

US 2007/0046948 A1 Mar. 1, 2007

(30) Foreign Application Priority Data

Aug. 26, 2005 (GB) ................................. 0517465.1

(51) Int. Cl.
*G01B 9/02* (2006.01)
(52) U.S. Cl. ..................................................... 356/479
(58) Field of Classification Search ................. 356/450, 356/477, 479, 497; 250/227.19, 227.27; 351/206; 385/12
See application file for complete search history.

(56) References Cited

U.S. PATENT DOCUMENTS

| | | | |
|---|---|---|---|
| 5,321,501 A * | 6/1994 | Swanson et al. ............ | 356/479 |
| 5,459,570 A | 10/1995 | Swanson et al. | |
| 5,469,261 A | 11/1995 | Hellmuth et al. | |
| 5,491,524 A | 2/1996 | Hellmuth et al. | |
| 5,493,109 A | 2/1996 | Wei et al. | |
| 5,537,162 A | 7/1996 | Hellmuth et al. | |
| 5,777,719 A * | 7/1998 | Williams et al. ............ | 351/212 |
| 5,975,697 A * | 11/1999 | Podoleanu et al. .......... | 351/206 |
| 6,379,005 B1 * | 4/2002 | Williams et al. ............ | 351/211 |
| 6,588,900 B1 | 7/2003 | Le Gargasson et al. | |
| 2003/0025874 A1 | 2/2003 | Williams et al. | |
| 2003/0053026 A1 | 3/2003 | Roorda | |
| 2003/0199769 A1 | 10/2003 | Podoleanu et al. | |

(Continued)

FOREIGN PATENT DOCUMENTS

FR 2 865 371 7/2005

(Continued)

OTHER PUBLICATIONS

Great Britian Office Action; No. GB0517465.1; Examiner: MacDonald; Date: Nov. 8, 2005.

(Continued)

*Primary Examiner*—Michael A. Lyons
(74) *Attorney, Agent, or Firm*—Nixon Peabody LLP; Jeffrey L. Costellia

(57) ABSTRACT

Optical mapping apparatus for imaging an object, comprising an optical coherence tomography (OCT) system including an OCT source, an OCT reference path leading from the OCT source to an OCT receiver, an OCT object path leading from the object to the OCT coupler, an OCT depth scanner adapted to alter at least one of the OCT reference path and the OCT receiver path. A confocal system is provided including a confocal optical receiver a confocal path leading from the object to the confocal optical receiver via a confocal input aperture. An adaptive optics (AO) system is provided to correct optical aberrations in the OCT object path and the confocal path.

47 Claims, 8 Drawing Sheets

U.S. PATENT DOCUMENTS

2004/0239876 A1* 12/2004 Levine .................. 351/206

FOREIGN PATENT DOCUMENTS

| WO | WO 03/020121 | 3/2003 |
|---|---|---|
| WO | WO 03/105678 A2 | 12/2003 |
| WO | WO 2005/060823 A1 | 7/2005 |

OTHER PUBLICATIONS

Austin Roorda et al., "Adaptive Optics Scanning Laser Opthalmoscopy", Optics Express, May 6, 2002, vol. 10, No. 9, pp. 405-412.

Al-Chalabi, S.A. et al., Partially coherent sources in interferometric sensors, Dept of Electronic and Electrical Engineering, Apr. 26-28, 1983, pp. 132-135, University College London, England.

Zhang, Y. et al., Adaptive optics parallel spectral domain optical coherence tomography for imaging the living retina, Optics Express, Jun. 13, 2005, pp. 4792-4805, vol. 13, No. 12.

Fercher, A., Optical Cogerence Tomography, Journal of Biomedical Optics, Apr. 1996, pp. 157-173, vol. 1, No. 2.

Gilgen, H. et al., Submillimeter Optical Reflectometry, Journal of Lightwave Technology, Aug. 1989, pp. 1225-1233, vol. 7, No. 8.

Podoleanu, A. et al., Transversal and Longitudinal Images from the Retina of the Living Eye Using Low Coherence Reflectometry, Journal of Biomedical Optics, Jan. 1998, pp. 12-20, vol. 3, No. 1.

Sawatari, T., Optical Heterodyne Scanning Microscope, Applied Optics, Nov. 1973, pp. 2768-2772, vol. 12, No. 11.

Liang, J et al., Supernormal vision and high resolution retinal imaging through adaptive optics, J. Optical Society of America, Nov. 1997, pp. 2884-2892, vol. 14, No. 11.

Liang J. et al., Aberrations and retinal image quality of the normal human eye, J. Optical Society of America, Nov. 1997, pp. 2873-2883, vol. 14, No. 11.

Webb, R. et al., Confocal scanning laser ophthalmoscope, Applied Optics, Apr. 15, 1987, pp. 1492-1499, vol. 26, No. 8.

Huang, D et al., Optical Coherence Tomography, Science, Aug. 1, 1991, pp. 1178-1181, vol. 254.

Youngquist, R et al., Optical coherence-domain reflectometry: a new optical evaluation technique, Optics Letters, Mar. 1987, pp. 158-160, vol. 12, No. 3.

Podoleanu, A. et al., En-face coherence imaging using galvanometer scanner modulation, Optics Letters, Feb. 1, 1998, pp. 147-149, vol. 23, No. 3.

Podoleanu, A. et al., Simultaneous en-face imaging of two layers in the human retina by low-coherence reflectometry, Optics Letters, Jul. 1, 1997, pp. 1039-1041, vol. 22, No. 13.

Podoleanu, A. et al., Coherence imaging by use of a Newton rings sampling function, Optics Letters, Nov. 1, 1996, pp. 1789-1791, vol. 21, No. 21.

Albert, O. et al., Smart microscope: an adaptive optics learning system for aberration correction in multiphoton confocal microscopy, Optics Letters, Jan. 1, 2000, pp. 52-54, vol. 25, No. 1.

Hermann, B. et al., Adaptive-optics ultrahigh-resolution optical coherence tomography, Optics Letters, Sep. 15, 2004, pp. 2142-2144, vol. 29, No. 18.

Fercher, A., et al., Eye-length measurement by interferometry with partially coherent light, Optics Letters, Mar. 1988, pp. 186-188, vol. 13, No. 3.

* cited by examiner

__US 7,466,423 B2__

OPTICAL MAPPING APPARATUS

TECHNICAL FIELD OF THE INVENTION

The present invention relates to an optical mapping apparatus and to methods which can be used to supply high resolution images from essentially transparent objects or tissue simultaneously or, sequentially, via aberrated paths. Confocal, fluorescence and optical coherence tomography channels are provided. In particular, but not exclusively, the invention relates to the imaging of ocular tissue.

BACKGROUND OF THE INVENTION

In the description which follows, reference is made primarily to the eye as the object. This has to be understood as merely a way to help the description and not as a restriction of the application of the present invention. As such, where the term "eye" is used, a more general transparent and scattering object or organ may be sought instead. In the case of the eye, the object is the retina which is to be imaged via the anterior chamber which introduces aberrations. When a specimen in microscopy is the object, the aberrations are introduced by the microscope objective, the microscope slide or other intermediate plates and optics devices, or even by the superficial layers of the specimen.

Low coherence interferometry is an absolute measurement technique which allows high resolution ranging and characterisation of optoelectronic components as presented in the papers S. A. Al-Chalabi, B. Culshaw and D. E. N. Davies, "Partially coherent sources in interferometric sensors", *First International Conference on Optical Fibre sensors*, 26-28 Apr. 1983, I. E. E. London, pp. 132-135, 1983, R. C. Youngquist, S. Carr, and D. E. N. Davies, "Optical coherence-domain reflectometry: A new optical evaluation technique," *Opt. Lett.* 12(3), pp. 158-160 1987 and H. H. Gilgen, R. P. Novak, R. P. Salathe, W. Hodel, P. Beaud, Submillimeter optical reflectometry", *Lightwave Technol.*, Vol. 7, No. 8, pp. 1225-1233, 1989.

The first application in the biomedical optics field was for the measurement of the eye length as shown in A. F. Fercher, K. Mengedoht and W. Werner, "Eye length measurement by interferometry with partially coherent light", *Opt. Lett.*, Vol. 13, No. 3, (1988), pp. 186-189.

Adding lateral scanning to the scanning in depth, allows acquisition of 3D information from the volume of biological media. This concept, of adding devices for lateral scanning in an interferometer, has been presented in papers on heterodyne scanning microscopy, such as "Optical heterodyne scanning microscope", published by T. Sawatari in *Applied Optics*, Vol. 12, No. 11, (1973), pp. 2766-2772.

The potential of the technique for high resolution imaging of the tissue is often referred to as optical coherence tomography (OCT) as presented in D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, 'Optical coherence tomography', *Science* 254, pp. 1178-1181, 1991 and in the paper "Optical coherence tomography" by A. F. Fercher, in *J. Biomed. Opt.*, 1(2), (1996), pp. 157-173. OCT has the potential of achieving high depth resolution, which is determined by the coherence length of the source. For example, optical sources, such as superluminiscent diodes and mode-locked lasers are now available with coherence lengths below 20 μm.

An OCT apparatus is now commercially available, which produces longitudinal images only, i.e. images in the planes (x,z) or (y,z), where the z axis is perpendicular to the patient's face and x and y axes are in the plane of the patient's face. Examples of such apparatus for longitudinal imaging are described in U.S. Pat. Nos. 5,493,109, 5,537,162, 5,491,524, 5,469,261, 5,321,501 and 5,459,570.

In the documents and patents above, A-scans, which are axial reflectivity profiles are generated, and B-scan images are obtained by grouping together several A-scans for adjacent transverse position of the scanning beam. Different scanning procedures are explained in the patent application US20030199769A1.

OCT has also been reported as being capable of providing en-face, or transversal profiles, or T-scans, which are reflectivity profiles generated by moving the beam transversally across the target. Based on T-scans, constant depth images (C-scan, or images with the same orientation as in microscopy) can be generated, as reported in "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789-1791, "Simultaneous En-face Imaging of Two Layers in Human Retina" Opt. Letters, by A. Gh. Podoleanu, G. M. Dobre, D. J. Webb, D. A. Jackson, published in Opt. Lett., 1997, vol. 22, No. 13, pp. pp. 1039-1041, "En-face Coherence Imaging Using Galvanometer Scanner Modulation" by A. Gh. Podoleanu, G. M. Dobre, D. A. Jackson, Opt. Lett. 23, pp. 147-149, 1998 and in "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, 3(1), pp. 12-20, 1998. T-scan technology is also described in the U.S. Pat. No. 5,975,697.

The OCT technique applied to ophthalmology has evolved rapidly in the last few years, as it can deliver a much better depth resolution than a scanning laser ophthalmoscope (SLO), based on the confocal microscopy principle. The technology of SLO was presented in R. H. Webb, G. W. Hughes and F. C. Delori, "Confocal scanning laser ophthalmoscope," Applied Optics, 26, 1492-1499 (1987). SLOs deliver C-scan images.

The limitations of the longitudinal OCT imaging instruments have been addressed in two respects: (i) establishing procedures to generate en-face OCT images from the retina, as mentioned in the papers by Podoleanu mentioned above, and (ii) design of a dual channel OCT/confocal instrument for the eye, as disclosed in the U.S. Pat. No. 5,975,697.

However, important limitations still exist in imaging with high resolution the retina and tissue in histology. The transversal resolution in OCT imaging is governed by the optics of the eye and its aberrations. Adaptive optics was employed in a flood illuminated eye as described in US2003/0025874A1 and in J. Liang and D. R. Williams", Aberrations and retinal image quality of the normal human eye", JOSA A 14: (11) 2873-2883, (1997) and improved the transversal resolution to the point where it was possible to distinguish the cones in the fovea as shown in J. Liang, D. R. Williams, D. T. Miller, "Supernormal vision and high-resolution retinal imaging through adaptive optics", JOSA A 14: (11) 2884-2892, (1997). AO utilises two devices operating in closed loop. In the AO system, a wavefront sensor measures the aberrations by evaluating the phase distribution over a defined plane. This information is used to actuate a wavefront corrector to imprint distortions of opposite sign in order to convey an aberration free image to the display. A flying spot ophthalmoscope, (i.e. an ophthalmoscope using scanning the beam point by point and producing a display signal for each pixel where the spot is incident, in opposition to a fundus camera which flood illuminate the retina, incorporating AO elements was reported by A. Roorda, F. Romero-Borja, W. J. Donnelly III, H. Queener, T. J. Herbert and M. C. W. Campbell, "Adaptive optics scanning laser ophthalmoscopy", in Opt. Express, Vol. 10, No. 9, pp. 405-412, (2002) which achieved a resolutions of 2.5 μm transversal and 100 μm axial in the eye.

Adaptive optics was also reported in being used to compensate for the aberration in microscopy. Such a possibility is described in "Smart microscope: an adaptive optics learning system for aberration correction in multiphoton microscopy", by G. Albert et al, published in Opt. Letters, vol. 25, No. 1, January 2000, pp. 52, 54. Use of AO has lead to an increase of the image size by 9 times due to extending the useable areas of focusing elements close to the edges.

As mentioned above, OCT provides means for achieving a high resolution in depth for optical systems of low numerical aperture (NA). AO provides means to correct for the aberrations in the optical path and in this way, to improve both transverse and depth resolution, to the level allowed by the NA of the interface optics.

If solutions are found to combine the two technologies, OCT and AO, then high resolution could be achieved both in lateral and in depth directions. In this way the minimum resolved volume, the voxel, could be reduced.

The patent application WO2003/105678 A2 discloses a system where a wavefront corrector is used to compensate for the aberrations of the eye in a flood illuminated system incorporating an OCT channel. As a disadvantage of the system disclosed, both reference beam and object beam from the interferometer traverse the wavefront corrector. The reference beam is free of aberrations and there is no need to correct it, and in fact it will be practically aberrated by the corrector. Placing the wavefront corrector after the interferometer, the corrector sees two optical signals, object and reference. Both object and reference beams are routed via the wavefront corrector with disadvantages in terms of system complexity, and reduction in the corrector efficiency, as central actuators in the correctors are sacrificed to reflect the reference beam.

As another disadvantage, the OCT system in WO 2003/105678 operates as a full field time domain OCT, or coherence radar, where the 2D interference map of a reference local beam and an object beam returned from the object is displayed by a 2D CCD camera, which produces C-scan OCT images. It is known that flood illumination imaging of the fundus is inferior to flying spot in terms of signal to noise ratio. Flood illumination relies on the dynamic range of CCDs, which is maximum 16 bits. Coherence radar or full field OCT systems (as that in WO2003/105678 A2) can measure reflectivity not smaller than $10^{-5}$. The signal to noise ratio is in this way smaller than that possible to be achieved in flying spot OCT, which can in principle measure $10^{-14}$ reflectivity.

As another disadvantage, B-scan OCT images can only be produced after a stack of C-scan images have been collected from different depths, and by software means, a B-scan is inferred from the 3D volume of data, i.e. a B-scan cannot be produced in real time.

The paper *Adaptive optics parallel spectral domain optical coherence tomography for imaging the living retina* by Yan Zhang, Jungtae Rha, Ravi S. Jonnal, and Donald T. Miller, published in Opt. Express, Vol. 13, No. 12, Page 4792-4811 presents a combination of an AO system with a spectral domain OCT (SD-OCT) camera based on a free-space parallel illumination architecture. Again, the AO correction operates in the emergent beam only, and as in the system of WO 2003/105678, on both reference and object beams.

As another disadvantage of the Zhang system, the two images generated in sequential regime cannot be compared to each other. C-scan fundus flood illuminated images and B-scan OCT images are obtained sequentially. By removing the diffraction grating and replacing it with a mirror, the CCD in the system is used to read a C-scan image in the fundus camera regime instead of a dispersed optical spectrum in the spectral OCT regime. Because in one regime, fundus camera, a C-scan is generated while in the OCT regime, a B-scan image, due to their rectangular orientation, the two images are not compatible.

As another disadvantage of the Zhang system, the fundus camera regime demonstrates improvement in the transverse resolution of C-scan images when AO is applied, but because no confocal aperture is used, the depth resolution is larger than that achievable in a genuine confocal system.

Another disadvantage of the flood illumination used in the system and the system of WO 2003/105678, is that the rays enter and return from the eye, or from the microscope objective in microscopy, within a fan with an angular extension given by the size of the lateral image size on the retina, or on the specimen in microscopy respectively. These rays "see" different aberrations and the AO system can only compensate for an average of cumulated aberrations over the angular extension of the fan of rays. Therefore, a flood illuminated AO system requires a separate source to provide the optical beam for the wavefront sensor.

Also, flood illumination means that some scattering from adjacent points to a pixel reach the photodetector in the CCD array corresponding to that pixel generating cross talk and noise.

The paper Adaptive-optics ultrahigh-resolution optical coherence tomography, by B. Hermann, et al, published in Optics Letters, Vol. 28, No. 18, 2004, 2142-2144, presents a slow flying spot system OCT where the fast scanning direction is in depth. Using A-scans, B-scan images are generated. The systems disclosed in the paper by Zhang and Hermann above are based on A-scans. Therefore, such systems cannot build a C-scan image in real time. Such C-scan can only be produced after several B-scans are acquired and then by software means, C-scans are inferred. The orientation of B-scan images is rectangular to that of confocal microscopy images, which provides C-scan images. C-scan images are desirable, because they are familiar to ophthalmologists, as scanning laser ophthalmoscopes are being used from 1981. C-scan images are also familiar to the microscopy community, as their real time output is a raster image oriented in a constant depth plane. C-scan images have the same orientation as that of fundus cameras or microscopes and are easier to interpret than cross section, B-scan images. Therefore is disadvantageous not to be able to generate real time C-scan images, especially in cases of moving organs and fast processes in biology, where the C-scan inferred from a 3D data volume acquired over time is corrupted by movement.

As an additional disadvantage of such systems, a large depth of focus is required when collecting A-scans. A depth of focus comparable with the depth range, 1-2 mm when scanning the retina. If AO is applied, the confocal core of the OCT could ideally shrink to less than 100 μm, therefore A-scan will be modulated by the focus profile with maximum sensitivity within a 100 μm range and insignificant values outside.

As another disadvantage, the Zhang's and Hermann's papers above refer to a regime, where OCT B-scan images are obtained under a static mirror configuration. The aberrations are read, correction evaluated, memorised and then the AO loop is opened. This does not allow correction of aberrations in real time.

All documents above refer to improvements in either the OCT channel (WO 2003/105678, Hermann) or the confocal channel (Roorda) with no attention given to correspondence of images between the two configurations and the scanning possibilities are limited due to the specific embodiments proposed. Hermann's Optics Letters paper is a flying spot system, based on A-scan OCT profiles only, which excludes real time T-scans and real time C-scans. Roorda's paper refers to a flying spot system which produces a raster imaging, a C-scan system only, in an SLO, which cannot achieve B-scan images in real time. System of WO 2003/105678 is not compatible with OCT B-scan imaging, as the interface optics, the lenses between the source and the eye need to be changed to project a line instead of a raster on the eye.

Such configurations cannot provide pairs of OCT and confocal images at the same time.

U.S. Pat. No. 5,975,697 shows how based on T-scans, pairs of OCT and confocal images could be generated at the same time, in two regimes, B and C-scan. However, because the resolution is limited in the confocal channel, one image in the pair, the confocal, does not provide any depth resolution in the either B or C-scan regimes.

Therefore it is desirable to provide solutions for the problems listed above.

SUMMARY OF THE INVENTION

According to a first aspect of the invention, there is provided an optical mapping apparatus comprising: an optical coherence tomography (OCT) system including: an OCT source, an OCT reference path leading from the OCT source to an OCT receiver, an OCT object path leading from the object to the OCT receiver, and an OCT depth scanner adapted to alter at least one of the OCT reference path and the OCT object path so as to adjust an OCT optical path difference to enable the OCT system to obtain OCT image data from different axial depths within the object; a confocal system including: a confocal source, a confocal optical receiver, and a confocal path leading from the object to the confocal optical receiver, the confocal system being arranged to obtain confocal image data from the object; an adaptive optics (AO) system including: a wavefront corrector and a wavefront sensor, the adaptive optics system being arranged to transfer a wavefront sensing beam along a wavefront sensing path leading from the object to the wavefront sensor, and; wherein the apparatus is arranged such that there is a first common path shared by a portion of the wavefront sensing path, a portion of the OCT object path and a portion of the confocal path, and there is a second common path shared by a portion of the OCT object path and a portion of the confocal path, and wherein the adaptive optics system is adapted to correct for optical aberrations in the first common path by means of the actuation of the wavefront corrector under control of the wavefront sensor.

Some embodiments of the invention further comprise a scanner located in the second common path for scanning an optical beam from at least one of the OCT source and the confocal source over a predetermined area; interface optics for transferring an optical beam from said scanner to the object and for transferring an optical output beam reflected and scattered from the object back along said second common path through said scanning means.

In some embodiments, first focussing means is provided in the second common path, the first focussing means being arranged to focus light from the OCT source and/or the confocal source at different axial depths within the object for imaging. In some embodiments the first focussing means is arranged to adjust the focus synchronously with the use of the OCT depth scanner to adjust the OCT optical path difference. The first focussing means may comprise the wavefront corrector. In some embodiments the first focussing means is in a portion of the second common path that is not shared with the first common path.

In some embodiments, the OCT source is a low coherence source the first focusing element implements depth focus scanning for the said depth scanning required by the said B or C-scanning regime according to the following steps: (1) with no depth scanning, the AO system is used to evaluate and then correct for the aberrations in the at least first common path, step which proceeds with no or with T-scanning, (2) control signals towards the wavefront corrector are stored, (3) the link between the wavefront sensor and the wavefront corrector is interrupted, (4) focus adjusting signals are applied to the wavefront corrector, to modify the position in depth where both channels, confocal and OCT, focus and T-scans are collected from, while the same correction of aberrations according to the stored values in step 2 is maintained.

In some embodiments the first focusing element implements depth focus scanning for the said depth scanning required by the said B or C-scanning regime by applying adjusting signals via the AO electronic feedback link to the wavefront corrector to modify the position in depth where both channels, confocal and OCT focus and T-scans are collected from, while dynamically maintaining the correction of aberrations in the at least correcting path according to the instantaneous control signals derived by the wavefront sensor while T scanning is performed.

In some embodiments, the first focusing element comprises apart from the wavefront corrector, of a focusing element within the interface optics which adjusts the convergence of the optical beam via it according to controlling signals applied to an interface optics driving input, which implements depth focus scanning for the said depth scanning required by the said B or C-scanning regime according to the following steps: (1) with no depth scanning, the AO system is used to evaluate and then reduce the aberrations in the at least correcting path, step which proceeds with no or with T-scanning, (2) control signals towards the wavefront corrector are memorised, (3) the link between the wavefront sensor and the wavefront corrector is interrupted, (4) focus adjusting signals are applied to the interface optics driving input, to modify the position in depth where both channels, confocal and OCT focus and T-scans are collected from, while the same correction of aberrations according to the stored values in step 2 is maintained.

In some embodiments the wavefront sensor comprises a wavefront sensor focussing element and a photodetector array, the wavefront sensor focussing element being arranged to adjust the focus of light transferred onto the wavefront sensor so as to select different axial depths within the object for imaging. The wavefront sensor focussing element may comprise an axially moveable lenslet array. The wavefront sensor focussing element may comprise a lenslet array with an electronically variable focal length.

In some embodiments the wavefront sensor focusing means implements depth focus scanning for the depth scanning required by the said B or C-scanning regime by applying adjusting signals to a lenslet array to modify the position in depth where both channels, confocal and OCT focus and T-scans are collected from, while dynamically maintaining the correction of aberrations in the at least correcting path according to the instantaneous control signals derived by the wavefront sensor while T scanning is performed.

In some embodiments the apparatus comprises an OCT/confocal splitter arranged to split light from the object transferred via the second common path into an uncommon OCT path that is portion of the OCT path that is not common with the confocal path and into an uncommon confocal path that is not common with the OCT path.

The OCT and confocal source could be a shared low coherence source. In which case, the object could generate fluorescence and the OCT/confocal splitter may be dichroic to allow the majority of OCT output beam from the object to reach the OCT receiver and the majority of beam due to fluorescence reach the confocal receiver. A supplementary filter may be inserted in the uncommon confocal path to reduce the strength of the excitation source beam.

A second focussing element may be provided in the uncommon confocal path, the second focussing element being arranged to focus light from the confocal source that has been reflected from the object at different axial depths within the object for confocal imaging. The second focussing element may be arranged to adjust the focus synchronously with using the OCT depth scanner to adjust the OCT optical path difference. The second focussing element may be adapted to enable independent control of the axial depth within the object from which the OCT image data is obtained and the axial depth within the object from which the confocal image data is obtained.

In some embodiments a third focussing element is provided in the uncommon OCT path, the third focussing element being arranged to focus light from the OCT source that has been reflected from the object at different axial depths within the object for OCT imaging. The third focussing element may be arranged to adjust the focus synchronously with using the OCT depth scanner to adjust the OCT optical path difference. The third focussing element may be adapted to enable independent control of the axial depth within the object from which the OCT image data is obtained and the axial depth within the object from which the confocal image data is obtained.

In some embodiments the depth scanning required by B or C-scanning regimes is achieved by applying adjusting the focussing means to modify the position in depth where both channels, confocal and OCT focus and T-scans are collected from, while maintaining the correction of aberrations in the at least correcting path according to the control signals derived by the wavefront sensor.

In some embodiments the depth scanning required by the said B or C-scanning regime is achieved by applying adjusting signals to the focussing means to modify the position in depth where the OCT channel focuses, while the position in depth where the confocal channel focuses is kept constant, and T-scans are collected in both channels, while maintaining the correction of aberrations in the at least correcting path according to the control signals derived by the wavefront sensor.

In some embodiments the depth scanning required by the said B or C-scanning regime is achieved by applying adjusting signals to the focussing means to modify the position in depth where both channels, confocal and OCT focus and T-scans are collected from, while maintaining the correction of aberrations in the at least correcting path according to the control signals derived by the wavefront sensor.

In some embodiments the OCT and confocal systems collect light via fibre optic apertures, conjugate to each other via the OCT/confocal splitter and where a focusing element in the second shared path is moved axially by a driver according to controlling signals, and in this way, focus is changed simultaneously in the OCT and confocal channels.

In some embodiments the OCT and confocal systems collect light via fibre optic apertures, conjugate to each other via the OCT/confocal splitter and where the focusing element in the second common path has a variable focal length according to applied controlling signals, and in this way, focus is changed simultaneously in the OCT and confocal channels. Depth scanning required by the said B or C-scanning regimes may be achieved by applying adjusting signals to the focusing element in the second common path to modify the position in depth where the OCT channel focuses and confocal channel focuses, and T-scans are collected in both channels, while maintaining the correction of aberrations in the at least correcting path according to the control signals derived by the wavefront sensor.

In some embodiments, the scanner comprises a line scanner and a frame scanner. The scanner may be arranged so as to enable the apparatus to produce T-scans of the object for at least one of the OCT system and confocal system.

In some embodiments the apparatus is arranged to produce C-scans for at least one of the OCT system and confocal system by combining a number of different T-scans from a predetermined depth in the object. The apparatus may be arranged to produce B-scans for at least one of the OCT system and confocal system by combining a number of different T-scans from different axial depths in the object. The start depth and end depth for generating the B-scans for the OCT system and the confocal system may be independently controlled.

In some embodiments the apparatus comprises an OCT display for generating and processing an image from the image data obtained by the OCT system. The image generated by the OCT display may be a T-scan, a C-scan or a B-scan.

In some embodiments the apparatus comprises a confocal display for generating and processing an image from the image data obtained by the confocal system. The image created by the confocal system may be a T-scan, a C-scan or a B-scan.

In some embodiments the apparatus comprises an OCT display for generating and processing an OCT image from the image data obtained by the OCT system and a confocal display for generating and processing a confocal image from the image data obtained by the confocal system. The OCT image and the confocal image may be a T-scan, a C-scan or a B-scan. The apparatus may be arranged to simultaneously display the OCT image and the confocal image.

In some embodiments the OCT source is the same optical source as the confocal source. The same low coherence source could have a wavelength of 800 nm for imaging the eye ($\lambda_{OCT} = \lambda_C = \lambda_{WS}$)

In some embodiments the wavefront sensing path is arranged to lead from the object to the wavefront sensor via the corrector.

In some embodiments the apparatus further comprising a wavefront sensing source, the apparatus being arranged such that a wavefront sensing beam from the wavefront sensing source is transferred to the object and back from the object via the wavefront sensing path. The wavefront sensing source may not be the same source as either the OCT source or the confocal source. A wavefront sensor source focussing element may be provided in a path between the wavefront sensor source and the object, the wavefront sensor source focussing element being arranged to adjust the focus of light transferred onto the wavefront sensor so as to select different axial depths within the object.

In some embodiments the wavefront sensing path is arranged to lead from the object to the wavefront sensor not via the corrector.

In some embodiments a beam from the OCT source or the confocal source is transferred to the object and reflected so as to form the wavefront sensing beam.

In some embodiments the first common path and the second common path are shared paths up to a wavefront sensing splitter.

In some embodiments the confocal receiver is the same optical receiver as the OCT receiver. The apparatus may comprise a blocking member adapted to block light in the OCT reference path from reaching the shared confocal and OCT receiver so as to enable the confocal receiver to obtain confocal image data.

In some embodiments the said wavefront sensing beam returned from the object as well as the optical beam along the OCT object path are generated by the same low coherence source while a separate optical source is used in the uncommon confocal path to provide optical beam along the confocal path to be processed by the confocal system. The beam from the separate confocal source could be introduced into the uncommon confocal path using a dichroic confocal splitter and into the second common path using a dichroic OCT/confocal splitter to spectrally separate the beams from the said low coherence source and the said separate source. For example, $\lambda_{OCT}$ and $\lambda_{WS}$ could equal 1300 nm, with the wavefront sensor comprising a InGaAs camera, and $\lambda_c$ could equal 800 nm for skin and microscopy.

In some embodiments the OCT source is a low coherence source, while the wavefront sensing beam returned from the object as well as the confocal beam along the confocal path are generated by a separate source. The beam from the confocal and wavefront sensing source is introduced into the wavefront sensing path using a dichroic splitter and into the uncommon confocal path using a dichroic OCT/confocal splitter to spectrally separate the beams from the low coherence source and the confocal and wavefront sensing source. For example, $\lambda_{OCT}$ could be 1300 nm, while $\lambda_{WS}$ and $\lambda_c$ could be 800 nm for skin and microscopy.

In some embodiments the OCT source and the confocal source are the same low coherence source while a separate optical source is used to provide the said wavefront sensing beam. The beam from the wavefront sensing source said separate optical source could be introduced into the first common path using a dichroic splitter to spectrally separate the beams from the said low coherence source and the wavefront sensing source. A splitter could be provided to separate the first and second common paths, said splitter being dichroic to spectrally separate the beams from the said low coherence source towards the OCT and confocal receivers and the beam from the wavefront sensing source. For example, $\lambda_{OCT}$ and $\lambda_C$ could be 800 nm and $\lambda_{WS}$ could be 750 nm.

In some embodiments a dichroic splitter is introduced in the wavefront sensing path between the scanner and the object, and depth scanning required by the said B or C-scanning regime is implemented according to the following steps: (1) with no depth scanning, and with the scanner stopped in such a way that the wavefront sensing beam from the wavefront sensing source reaches the wavefront sensor, the AO system is used to evaluate and then correct for the aberrations in the first common path, (2) control signals towards the wavefront corrector are stored, (3) the link between the wavefront sensor and the wavefront corrector is interrupted, focus adjusting signals are applied to either the: said wavefront corrector, or to the interface optics driving input to modify the position in depth where both channels, confocal and OCT focus and T-scans are collected from, while the same correction of aberrations according to the stored values in step 2 is maintained.

In some embodiments the said wavefront sensing source and the OCT source are the same low coherence source while the confocal source is separate. For example, $\lambda_{OCT}$ and $\lambda_{WS}$ could be 1300 nm and $\lambda_c$ could be 800 nm.

In some embodiments the OCT source is a low coherence source while the wavefront sensing source and the confocal source are the same source. Light from the wavefront sensing source and the confocal source could be introduced in the first common path via a dichroic splitter. For example, $\lambda_{OCT}$ could be 1300 nm for skin, and $\lambda_{WS}$ and $\lambda_C$ could be 800 nm.

In some embodiments the OCT source is a low coherence source and the OCT/Confocal splitter is dichroic. For example, $\lambda_{OCT}$ could be 1300 nm for skin, and $\lambda_{WS}$ and $\lambda_C$ could be 1300 nm or 800 nm.

The process of adding AO elements splits the diagram of any OCT or of any OCT/Confocal system. The present discloses different possibilities to meld AO elements with confocal and OCT channels. The disclosure shows configurations with optimal placement of different optical components in three channels, OCT, confocal and AO to improve the lateral and depth resolution in both or in at least one channel, optical coherence tomography and/or confocal.

As another disadvantage of the systems discussed above, all the AO+OCT combined exploit the improvement in resolution in an OCT configuration only. Reducing the aberrations leads to improvements not only in the transversal direction, but in the axial direction as well, but this is obscured by the very narrow profile of the axial sampling profile in OCT. The improvement in the axial direction of the confocal core is not exploited in the documents mentioned above.

Also, none of the patents and document above make any provision for resolution enhancement of fluorescence images while providing improvement in an OCT configuration. Such images are of interest to indocyanine green and fluorescein imaging in the angiography of the eye and in the fluorescence microscopy of biologic samples. A system restricted to B-scan imaging is not suitable for examination of fluorescence, which is widely exercised in C-scan orientation.

Also, none of the patents and document above make any provision for adjusting the focusing away from that determined by the AO, required especially when the aberration of correction is closed to ideal and the much improved axial sectioning interval shrinks.

Embodiments of the invention improve the resolution of OCT images and/or fluorescence images by compensating for aberrations.

Losses

One of the main problem when imaging tissue, which returns little signal back, is to ensure efficiency in signal collection. The wavefront sensor requires tapping some of the signal returned from the object, so adding an AO channel will reduce the signal to OCT, and when signal is split to both an OCT and a confocal channel, it will reduce the signal to both. Signal from retina from instance could be as weak as $10^{-8}$ and minimisation of losses is paramount.

Therefore, the initial values of optimum splitting ratio of different beamsplitters in an OCT or in a combined OCT/confocal configuration need readjustment. In one of the aspect, embodiments of the present invention address this problem by: 1: Optimum design of splitting ratios; and 2: Using dichroic beamsplitters where possible, to conveniently route different wavelengths, however it is known that such filters affect the OCT sampling profile and pairing of wavelengths with filter transfer characteristics requires careful consideration.

Embodiments of the invention provide configurations, for 2 channels to share one wavelength and for the $3^{rd}$ to operate on a different wavelength to minimise the loss of signal.

Match of Beam Diameter at Different Optimum Points Along the Beam Towards the Object 1. Wavefront sensor has to cover with its area the pupil and be conjugated with the eye pupil, which dictates its spatial position in the beam, versus the placement in the beam of other elements such as transverse scanners and elements of the interface optics, including focusing elements. Therefore, in another aspect, embodiments of the invention provide solutions for the optimum position placement of the wavefront corrector and wavefront sensor and their combination with transverse scanners and interface optics elements to ensure minimum losses and focus compatibility.
2. The AO channel uses a wavefront corrector or several wavefront correctors which require that the beam in the eye pupil matches the size of the corrector. In optics, to transfer a beam of 3 mm, a mirror of 3, 5 or 10 mm, or any larger can be used and placed anywhere in a collimated beam. Routing the optical signal via a correcting deformable mirror requires the utilisation of all the corrector aperture. The more actuators that are used, the better the aberration correction. Also, its position in the beam is important, and it is desired that it is conjugated with the eye pupil (or the imaging focusing element in microscopy).

Embodiments of the invention provide a combination of confocal microscopy with OCT and AO, where the beam diameter is matched to that required by the wavefront corrector and wavefront sensor and these two components, wavefront corrector and wavefront sensor are placed at optimum different points along the beam towards the object, to ensure correction in both confocal and OCT channels.

Single Path and Double Path Aberration Correction

Wavefront correction could be introduced in single and double path configurations. In single path correction, the corrector operates on the beam emerging from the object but not on the beam going to the object. In such arrangement, the beam still suffers the aberration while propagating to the retina through the imaging focusing element, such as the eye lens. However, by using a very thin beam towards the eye pupil, aberrations are kept low because the beam is sent via the centre of the eye. The larger the beam diameter, the better the resolution, but the more observations collected. Therefore, for the returned beam, the eye pupil is kept large, 5-7 mm, in which case the beam cumulates aberrations and by correcting for these aberrations, transverse and depth resolutions corresponding to the large beam diameter value are possible to be achieved. In double path arrangement, the corrector responds to aberration introduced in the beam while propagating to the retina as well as to the aberration cumulated in the return path of the beam, in which case the beam diameter is generally the same for the incident and for the emerging beam. The single pass correction has advantages in terms of less aberrations to be collected and corrected for.

Therefore, in another aspect, embodiments of the invention provide for the combination of confocal microscopy with OCT and AO, which can operate in either single path or double path and embodiments which can allow both types of operation with the same configuration and the user has a choice, with no change of configuration to opt for single or dual path correction.

Chromatic Aberrations

Spectral behaviour of different optical components or tissue could lead to different aberrations at different wavelengths. Therefore it would be desirable to be able to collect, evaluate and correct for chromatic aberrations. In some embodiments, the wavelength for aberration correction can be conveniently chosen.

Compatibility of Operation as an Oct and Confocal Microscope with that of a Fluorescence Confocal Microscope The wavefront of the fluorescence signal is considered to be aberrated in the single path from the object through the imaging focusing element, therefore in a different aspect, the embodiments of the invention presents solutions for optimal combinations of single path and double path wavefront correction required when combining OCT and fluorescence imaging to provide simultaneous or sequential aberration free OCT and fluorescence images.

Narrowing of the Confocal Sectioning Profile in the OCT Channel

When the AO channel compensates for aberrations, axial resolution narrows to the level expected for an ideal focusing element in front of the object being imaged. This raises the problem of signal strength from depths outside the axial sampling profile of the confocal receiver at the core of the OCT channel. When imaging the retina, due to aberrations, the confocal core is known to have a depth sectioning profile not better than 300 µm. By applying AO, an axial profile as narrow as 50 µm could be achieved, interval smaller than the retina thickness. This shows that the improvement of the axial resolution due to AO may lead to a reduction of signal for depths outside the confocal profile. Embodiments of the invention provides solutions for addressing the problem of depth of focus shrinkage.

Focus Position in AO Versus the Desired Focus Position in OCT and Confocal Channels The AO channel may dictate a shift in the focusing towards the depth where the maximum signal originates from. For instance, when imaging the eye, a layer of highest reflectivity, such as the retinal pigment epithelium (RPE) determines the closed loop AO channel to focus at the depth where the RPE is. So, correcting for the aberrations has two effects, narrowing of the axial sampling profile and shift of such peak towards the depth dictated by the AO channel.

Dynamic focus procedure comprises moving the focusing depth in the confocal core of the OCT in synchronism with the coherence gate, and in this way selecting signal in the OCT from that depth where the two optical paths, in the object and reference paths are matched. However, in an OCT equipped with dynamic focus, after adding the AO system, it is difficult to predict the operation of the dynamic focus. The corrector fixes the best focus at the depth of the RPE level while the dynamic focus tries to move the focus at different depths in synchronism with depth scanning as required for generation of B or C-scans.

Embodiments of the invention provide solutions for addressing the conflict between the wavefront corrector and dynamic focus, in order to maximise the strength of signal in both channels and even more, select the depth where such strength is maximum for diagnostic reasons.

Generation of Depth Resolved T-scans in the Confocal Channel

By applying AO to a confocal SLO, an axial profile as narrow as 50 μm could be achieved, interval smaller than the retina thickness. Therefore, B-scan imaging is achievable in a confocal channel with depth resolution comparable to that of OCTs under SLD illumination. This also makes possible collection of depth resolved C-scans in the confocal channel. Embodiments of the invention enable simultaneous or sequential pixel to pixel correspondence depth resolved images can be collected in both channels, OCT and confocal, under compensation of aberrations.

In yet another aspect embodiments of, the invention shows provide a simultaneous confocal image with the OCT image, by providing configurations where three channels are optimally combined: OCT, confocal and AO.

Guidance of the C-scanning Via Confocal Scanning

Confocal C-scan images was used to guide OCT image acquisition along the transverse coordinate only. By being able to resolve structure in depth, the confocal image in such conventional arrangements looked like a superposition of all C-scans collected in the OCT channel. By applying AO, the C-scan of the retina could be "thinned" to 50 μm. Therefore, embodiments of the invention enable a confocal image to be efficiently used to guide the acquisition of a OCT image not only transversally but axially too.

Use of the Confocal Channel at the OCT Core to Deliver Sequentially a Confocal Image Confocal microscopy can take advantage of the depth resolution improvement due to AO more than OCT. Therefore, to exploit the full potential offered by AO, it is possible to implement a confocal imaging channel using the optical elements of the OCT channel. Therefore, in a different aspect, embodiments of the invention enable a confocal imaging channel to be implemented in a combined OCT-AO system. The invention provides solutions for sequential OCT and confocal regimes where similar orientation of images is again produced, with no alteration of elements in the path leading to the object to ensure enable pixel to pixel correspondence in the OCT and confocal regime.

Embodiments of the invention provide configurations which can provide images with the same orientation in both channels, confocal and OCT.

While wavefront correction improves resolutions in confocal microscopy as well as in OCT, no prior art exists in showing how such combination is achievable to make the most from wavefront correction. Embodiments of the invention provide configurations capable of generating B-scan OCT images and C-scan OCT images in real time, as well as generating B-scan confocal images and C-scan confocal images in real time, not possible to be achieved with any conventional configurations, in either simultaneous or sequential regime.

According to a second aspect of the invention, there is provided an optical mapping apparatus for imaging an object, comprising: an optical coherence tomography (OCT) system including: an OCT source, an OCT reference path leading from the OCT source to an OCT receiver, an OCT object path leading from the object to the OCT receiver, and an OCT depth scanner adapted to alter at least one of the OCT reference path and the OCT object path so as to adjust an OCT optical path difference to enable the OCT system to obtain OCT image data from different axial depths within the object; an adaptive optics (AO) system including: a wavefront corrector and a wavefront sensor, the adaptive optics system being arranged to transfer a wavefront sensing beam along a wavefront sensing path leading from the object to the wavefront sensor, and; wherein the apparatus is arranged such that there is a first common path shared by a portion of the wavefront sensing path, and a portion of the OCT object path, and wherein the adaptive optics system is adapted to correct for optical aberrations in the first common path by means of the actuation of the wavefront corrector under control of the wavefront sensor, the apparatus further comprising: a first focussing means provided in the first common path, the first focussing means being arranged to focus light from the OCT source at different axial depths within the object for imaging, wherein the first focussing means comprises the wavefront corrector.

In some embodiments the first focussing means is arranged to adjust the focus synchronously with the use of the OCT depth scanner to adjust the OCT optical path difference. The wavefront sensor may comprise a wavefront sensor focussing element and a photodetector array, the wavefront sensor focussing element being arranged to adjust the focus of light transferred onto the wavefront sensor so as to select different axial depths within the object for imaging. The wavefront sensor focussing element may comprise an axially moveable lenslet array. The wavefront sensor focussing element may comprise a lenslet array with an electronically variable focal length.

In some embodiments the apparatus further comprising a wavefront sensing source, the apparatus being arranged such that a wavefront sensing beam from the wavefront sensing source is transferred to the object and back from the object via the wavefront sensing path. The wavefront sensing source may not be the same source as the OCT source.

In some embodiments a wavefront sensor source focussing element is provided in a path between the wavefront sensor source and the object, wavefront sensor source focussing element being arranged to adjust the focus of light transferred onto the wavefront sensor so as to select different axial depths within the object.

The image data generated by the OCT system may be used to generate a T-scan, a C-scan or a B-scan.

According to a third aspect of the invention, there is provided an optical mapping apparatus for imaging an object, comprising: a confocal system including: a confocal source, a confocal optical receiver, and a confocal path leading from the object to the confocal optical receiver, the confocal system being arranged to obtain confocal image data from the object; an adaptive optics (AO) system including: a wavefront corrector and a wavefront sensor, the adaptive optics system being arranged to transfer a wavefront sensing beam along a wavefront sensing path leading from the object to the wavefront sensor, and; wherein the apparatus is arranged such that there is a first common path shared by a portion of the wavefront sensing path and a portion of the confocal path, and wherein the adaptive optics system is adapted to correct for optical aberrations in the first common path by means of the actuation of the wavefront corrector under control of the wavefront sensor, the apparatus further comprising: a first focussing means provided in the first common path, the first focussing means being arranged to focus light from the confocal source at different axial depths within the object for imaging, wherein the first focussing means comprises the wavefront corrector.

In some embodiments, the wavefront sensor comprises a wavefront sensor focussing element and a photodetector array, the wavefront sensor focussing element being arranged to adjust the focus of light transferred onto the wavefront sensor so as to select different axial depths within the object for imaging. The wavefront sensor focussing element may comprise an axially moveable lenslet array. The wavefront sensor focussing element may comprise a lenslet array with an electronically variable focal length.

In some embodiments the apparatus further comprises a wavefront sensing source, the apparatus being arranged such that a wavefront sensing beam from the wavefront sensing source is transferred to the object and back from the object via the wavefront sensing path. The wavefront sensing source may not the same source as the confocal source.

In some embodiments a wavefront sensor source focussing element is provided in a path between the wavefront sensor source and the object, the wavefront sensor source focussing element being arranged to adjust the focus of light transferred onto the wavefront sensor so as to select different axial depths within the object.

The image data generated by the confocal system may be used to generate a T-scan, a C-scan or a B-scan.

BRIEF DESCRIPTION OF THE DRAWINGS

The above and further advantages of the present invention may be better understood by referring to the following drawings.

DETAILED DESCRIPTION OF THE INVENTION

Figure 1:
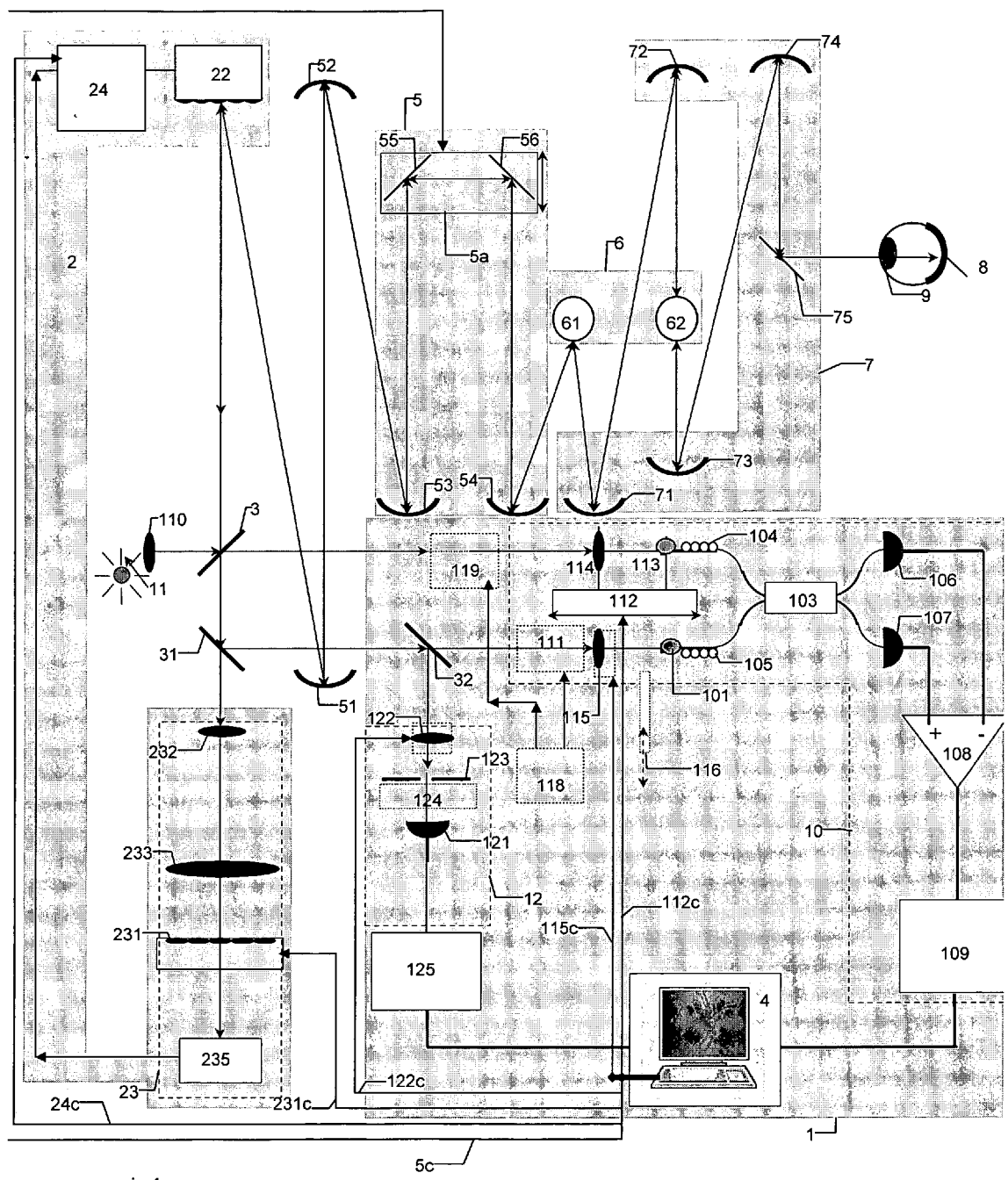
FIG. 1 shows a first embodiment of the system for high resolution imaging of an object via an aberrated path.

FIG. 1 shows a first embodiment of the high resolution imaging system according to an embodiment of the invention. Light from a low coherence source 11 is collimated via focusing element 110 and divided by an OCT beamsplitter, 3 into two beams, a reference beam and an object beam. The object beam is sent towards a wavefront corrector 22, wherefrom the beam is transferred via the a telescope, equipped with curved mirrors 51, 52 towards focusing optics 5, constructed from curved mirrors 53, 54 and flat mirrors 55, 56 in a Badal configuration. The object beam is then sent to a transverse scanner 6, constructed from a line scanner 61 and a frame scanner 62. The scanner 6 is arranged to scan beams from the source 11 over a predetermined area. Interface optics 7, consisting of curved mirrors 71-74 and flat mirror 75 are provided to transfer a beam from the scanner 6 to the object to be imaged, 8. The curved mirrors 51-54 and 71-74 could be parabolic or spherical. In FIG. 1, the object 8 is the retina behind the imaging focusing element, which in FIG. 1 is the anterior chamber of an eye. In this case the imaging element 9 represents the compound focusing achieved by the cornea and the eye lens. For applications in microscopy, the object 8 could be a microscope specimen while the imaging focusing element 9 is a microscope objective. Light back-reflected from the object 8 is transferred via the interface optics 7, transverse scanner 6 and focusing optics 5 back to the wavefront corrector 22 and via the OCT beamsplitter 3, towards a beamsplitter 31. Beamsplitter 31 sends a fraction of the light provided to it towards a beam-splitter OCT/confocal 32 and to a wavefront sensor 23. The wavefront corrector 22 is controlled by the wavefront sensor 23, via the feedback loop electronic processing circuit 24. The wavefront sensor 23, wavefront corrector and the feedback loop electronic processing circuit 24 constitute a closed loop AO system 2.

In all embodiments, the wavefront sensing source receives a wavefront sensing beam, and it will be appreciated that the circuit 24 processes information output from the wavefront sensor 23 relating to the aberrations collected by the wavefront sensing beam. The wavefront sensor 23 therefore can control the actuation of the wavefront corrector via the circuit 24 and the feedback loop so as to correct for aberrations.

The imaging instrument, 1 contains an OCT and a confocal channel. The reference beam from the source 3 is sent via a reference path towards the fibre input 113 of a balanced splitter 103, implemented in single mode fibre as a single mode directional coupler in FIG. 1. The optical path from the source 3 to the balanced splitter 103 forms the reference path for the OCT channel. Light is launched into the reference input 113 of the coupler 103 using a focusing element 114.

To keep the losses low, most of the light, for instance 90-96% from the OCT/confocal beam-splitter 32, is sent towards the object fibre input 101 of the splitter 103, focused by a focusing element 115.

Polarisation controllers, 104 and 105 match the polarisation from the two input apertures 101 and 102. The object beam interferes with the reference beam in 103 and the strength of the interference signal is read by a balanced receiver equipped with photodiodes 106 and 107 and differential amplifier 108. The signal is then processed in an OCT signal processing unit, 109, which creates a signal proportional with the strength of the interference signal, either in linear or logarithmic format. Phase information could also be recovered by conventional means and implemented in the signal processing unit, 109.

A small fraction of the beam input to the splitter 32 is sent towards the input aperture of a confocal receiver 12. The confocal receiver uses a high sensitive photosensor, 121, such as an avalanche photodiode or a photomultiplier tube, behind a focusing element 122 and an aperture 123. The confocal receiver can use a pinhole or the aperture of a fibre and different versions are known, such as these detailed in U.S. Pat. No. 6,769,769. The signal delivered by the photosensor 121 is amplified and processed in an amplifier unit 125 to supply a confocal channel image.

It will be apparent to those skilled in the art that where beam-splitters are in fibre as discussed, equally they could be implemented in bulk and vice-versa.

The signals from the two electronic units 125 and 109 are sent to a dual input display unit 4, which may incorporate a computer system such as a personal computer (PC) which controls the regimes of operation of the system, the type of scanning, its sequence of operation and data acquisition. The display unit 4 is arranged to process and display images produced by the OCT channel and the confocal channel.

The path starting after the beamsplitter 3, along the wavefront corrector 22, the focussing elements, the scanner 6 and the interface optics 7 to the object 8, and then back via the same elements towards the beam splitter 3, then via splitter 31 and to the coupler 103 constitutes an object path. The coupler 103 represents one of many possible OCT optical receivers, as will be appreciated. Interference in the OCT channel is obtained when the length of the reference path matches the length of the object path. Scanning of the optical path difference to generate B-scan images, or collect C-scan images from different depths is accomplished with a translation stage 112, which moves the fibre end 113 and the focusing element 114. Other possibilities are known to implement depth scanning in OCT, such as using a transmissive spectral scanning delay line, as described in the GB application No 0419383.5.

The wavefront sensor 23 could operate in the conventional manner, and could be implemented as a Shack Hartman device as described in paper by J. Liang, B. Grimm, S. Goelz and J. F. Bille, "Objective measurement of wave aberrations of the human eye with the use of a Hartmann-Shack wavefront sensor", J. Opt. Soc. Am. A., Vol. 11, No. 7, (1994), pp. 1949-1957. This may incorporate a lenslet array, 231, behind focusing elements 232, 233 acting as telescope to adapt the size of the incoming beam to that of the lenslet array. Light from the lenslet array is focused onto a 2D photodetecting array, 235, such as a CCD. The wavefront sensor could equally well be based on any other principle of wavefront sensing such as interferometry, phase diversity, curvature sensing or other methods of slope sensing such as embodied in the pyramid wavefront sensor.

The path from the object 8 via scanners 6, interface optics 7, wavefront corrector 22 up to the lenslet array 231 forms a wavefront sensing path.

The path from the object 8 via scanners 6, interface optics 7, wavefront corrector 22 up to the coupler 103 forms an OCT object path.

The path from the object 8 via scanners 6, interface optics 7, wavefront corrector 22 up to the pinhole or fibre input 123 forms a confocal path.

The intersection of wavefront sensing path, OCT path and confocal path forms a common 3-path. The path between beamsplitters 31 and 32 forms an uncommon 2 path, while the path between the splitter 32 and the coupler 103 forms an uncommon OCT path and that between the splitter 32 and the confocal input aperture 123 an uncommon confocal path.

The wavefront corrector 22 could operate according to a conventional manner of adaptive optics, and could be implemented as a deformable mirror, based on piezoelectric or electrostrictive materials, or using bimorph devices, magnetic force devices, or MEMS. Liquid crystals working in transmission have also been developed for this application, as described in G. T. Bold, T. H. Barnes, J. Gourlay, et al, "Practical issues for the use of liquid crystal spatial light modulators in adaptive optics", Opt. Commun. 148 (4-6): 323-330, Mar. 15 (1998). The corrector, wavefront sensor 23 and input aperture of the OCT channel and of the confocal receiver are all generally different from the eye pupil or microscope objective's aperture. In FIG. 1, the OCT aperture is determined by the diameter of the emergent beam from fibre at the position where element 115 is, if light was sent from one of the two outputs connected to photodetectors 106 and 107. Standalone OCT systems generally operate with small diameter beams, 2-3 mm in order to obtain images from the retina with un-dilated eyes. AO systems for the eye are used to compensate aberrations from within larger diameter pupils, is 4-7 mm. Conventional AO correctors vary in diameter from a few mm up to over a few cm. Conventional wavefront sensors for instance, when based on CCD cameras, have apertures depending on the CCD chip. Therefore, incorporating all these elements in the same optical path require adaptation of the beam diameter and careful consideration on their positioning in such a way, that the corrector and the wavefront sensor are conjugate to the imaging focusing element, the eye pupil, while the retina is conjugate with the input fibre, 101, in the OCT and the pinhole of fibre input 123 in the confocal channel.

Matching of beam diameter is achieved by telescopes equipped with lenses or mirrors, spherical or parabolic. It is known that such telescopes introduce their own aberrations and losses. Generally OCT system use single mode fibres while confocal channel may use a pinhole. This means that the numerical aperture (NA) of the OCT input aperture is approximately 0.1 while the NA of the confocal channel could be much larger. Therefore, there is scope in implementing different embodiments, where the size of different elements may suggest separation of the input paths leading to the OCT channel and to the confocal channel and interleaving other system components between them. By doing so, the number of telescopes in the system which match the size of different optical components is reduced with consequence in lowering the internal aberrations and losses in the system. An optimum number of telescopes should also be used, to minimize aberrations, for instance an even number is recommended. In FIG. 1, the position of the corrector 22 is conjugate with the pupil of the imaging focusing element 9 and with the two transverse scanners, 61 and 62. In FIG. 1, as one of the multiple possibilities, parabolic mirrors are used and their radius is adjusted to achieve desired beam diameters at different points. For instance, focusing element 110 could be a microscope objective or a telescope which in conjunction with the NA of fibre produces a beam diameter of 9.2 mm, matching the diameter of a conventional commercial 37 actuators mirror corrector, 22. The intermediate elements up to the first scanner, 61, reduce the diameter to 2.3 mm and the next elements increase it again to that of the pupil to be used, i.e. for instance 7 mm.

While a system combining an OCT system with confocal microscopy can tolerate grouping the line and frame scanners into a 2D compact scanner, it is desirable that this be avoided in a system of low aberrations, as that required for a system incorporating AO elements. This is why the scanners 61 and 62 are separated and interleaved with interface optics elements in FIG. 1. The absence of scanning aberrations makes the operation of the wavefront sensor 23 and of the wavefront corrector 22 easier. This is because the relative distance between the two transverse scanners 61 and 62 when grouped together lead to a distortion of the wavefront within the image raster. If the line scanner is placed in conjugate point with the eye pupil, then constant phase is obtained along the line in the raster, but the raster is curved along the frame direction. Furthermore, if the frame scanner is conjugate to the eye pupil, then the wavefront is flat along the frame scanning direction and curved along the line scanning direction. If transverse scanners are not separated and interleaved with focusing elements to have them both conjugate to the eye pupil, then the system aberrations pulsate with the transverse scanning. This would impose a further constraint on the aberrations corrections.

Frame scanners are slower and consequently, their mirror size is larger than that of line scanners which are faster. This means that a telescope may be placed between the two transverse scanners and suitable size correctors can be placed here too. In this embodiment, the wavefront sensor 23 is placed in the beam returning form object after the corrector 22, i.e. the corrector 22 is closer to the eye than the wavefront sensor as well. For instance, the components could be mounted in the following order (from the source) with a large size corrector:

corrector 22, frame scanner 61, telescope to reduce the beam diameter to the aperture of the line scanner 61 and the eye pupil. Equally possible is the sequence: frame scanner 62, corrector 22, telescope, line scanner 61. A problem remains with accommodating a large diameter beam, of over 1 cm, into a single mode fibre of 5.5 μm core usually with 0.12 NA. This requires another telescope to reduce the beam diameter to values which allows efficient injection into the single mode fibre, which may be introduced before the focusing element 115 (not shown).

The comments above show that a wavefront sensor 23 and a corrector 22 cannot simply be placed in any point of the object beam in a given OCT system or combined OCT/confocal system to obtain an OCT/AO or an OCT/C/AO system respectively. It is desired that their positions be optimally chosen to satisfy conjugation with eye pupil and within parts of the object beam with corresponding diameters.

As a possible alternative, if the corrector 23 can operate as fast as the frame scanner 62 (i.e. 1-10 Hz), then grouping of the line scanner 61 and frame scanner 62 into a compact XY transversal scanning head could be tolerated. In such cases, calibration is used prior to imaging, where a curve of compensation parameters is stored versus the angle of the frame scanner which is subsequently used in the aberration compensation process when scanning the eye or the specimen.

At the level of current technology, AO wavefront sensors and actuators can operate at rates over 1 kHz, therefore it is possible to operate them to dynamically compensate the aberrations while scanning along the line in the raster. Once such fast elements are in place, correction could be applied dynamically along X and Y in the raster, at 500 Hz in the line and at 2 Hz in the frame, rates known for current T-scan OCT systems.

Another problem is connected to the carrier required to transfer the information on tissue reflectivity, into brightness in the final OCT image. This carrier could be created by an external phase modulator or by the path modulation introduced by the very process of transversal scanning. In order to see smaller pixels in the image when using AO, the image size is generally much smaller, e.g. a few degrees, than that used in conventional clinical OCT and SLO systems, which are typically 40 degrees or more. Therefore, the frequency of the carrier created by the very process of transverse scanning may be so low, that it is rejected by the high pass filter within the electronic processing unit 109, used to reduce the 1/f noise after the photodetectors 106, 107. The carrier results by scanning the beam over a virtual sampling function, as described in the papers by Podoleanu mentioned above. The same papers show that the sampling function depends on the object as well as on the adjustment of the beam in relation to the scanning mirrors. For an aberration-free system, when the object is a mirror, the sampling function is in the form of Newton rings. If the mirror is replaced by a collection of scatterers, their spatial pattern modulates the Newton rings sampling function, which distorts the shape of the rings until disappearance. The result is B-scan and C-scan images, with speckle where fringes are superposed over the shape of scatterers, shape which determines the morphologic structure. To reproduce the shape of scatterers, the fringe pattern has to be eliminated, as this fringe pattern takes the role of the sampling function in Podoleanu's papers when the object was a mirror. If only a few fringes are superposed over the shape of the scaterrer, by scanning the beam over this fringe pattern, the frequency generated may be too small to be passed by the high pass filter within signal processing unit 109. Only a sufficient number of fringes over a scattering feature would reproduce correctly the shape of the feature. Therefore, to benefit from the increase in the transversal resolution brought by the AO, the spatial period of the sampling function in the OCT channel should be smaller than the AO improved transversal resolution. This could be achieved by fast phase modulation of the optical path in the interferometer to phase modulate the fringe pattern at a rate faster than that of T-scanning. For instance, for a strength of the phase modulation equivalent to a path modulation of λ/4, the bright fringe is replaced with a dark fringe. Doing this sufficiently fast, will generate a high frequency, which when larger than the T-scanning rate can be demodulated with a band pass filter tuned to the phase modulation frequency. For instance, for a 500 Hz T-scan, and a small size of 100 pixels, at least 400 kHz is required. This can be obtained by using electro-optic or acousto-optics modulators. It is known that introduction of such modulators in a low coherence reflectometer leads to dispersion problems. Uncompensated dispersion spoils the depth sectioning profile of the OCT channel. This shows the interrelation of problems to be addressed when blending en-face OCT with AO.

Two possible solutions are envisaged:

1. Use of an electro-optic phase modulator in conjunction with dispersive compensation elements, either a similar modulator in the other arm of the interferometer; or a scanning delay line using at least a dispersion element, a focusing element and a tilted mirror, as shown in. GB application No 0419383.5. FIG. 1 shows two phase modulators, 119 and 111 driven by generators 118. To generate a carrier frequency of 1 MHz, only one modulator can be driven with the other used to compensate for dispersion. When Bragg cells are employed, they are excited at 40 or 80 MHz., therefore to bring the carrier frequency down, one is excited at 81 and the other at 82 MHz, with the beat, 1 MHz being the carrier. The OCT system in FIG. 1 can use a phase modulator, such as an electro-optic modulator, an acousto-optic modulator placed in one arm of the OCT interferometer, or two could be placed in the same arm, but preferably one in each arm of the interferometer for better compensation of dispersion.

2. Use of a scanning delay line consisting of at least a dispersion element, a focusing element and a fast galvo-mirror, preferably a resonant scanner, as shown in the GB application No 0419383.5, to create a high sufficient carrier frequency by shifting the beam away from the pivot of the fast vibrating mirror.

Two possible regimes depending on the phase modulation used:

1. However, path modulation introduced by the transverse scanner determining the line in the raster could still be used on its own, in which case phase modulators 119 and 111 are not necessary and this is why they are shown dashed in FIG. 1. In this case, an improvement in the signal to noise ratio is expected when closing the AO loop, but less improvement in the transversal pixel size than in the case of using an external phase modulator.

2. When using external phase modulation, improvement in both the OCT signal strength and transverse resolution is expected.

A summary of the improvements after applying the AO is presented for eye imaging and confocal microscopy in table 1.

TABLE 1

Improvements due to AO on the two channels. YES means that by applying aberration corrections, the parameter, signal strength or resolution improves

| Type of application | Carrier generated by | OCT channel | | | Confocal channel | | |
|---|---|---|---|---|---|---|---|
| | | Signal strength | Transverse resolution | Depth resolution | Signal strength | Transverse resolution | Depth resolution |
| Eye (low NA imaging) | No external phase modulator | YES | Speckle | Dynamic focus required | YES | YES | YES |
| | Using an external phase modulator | YES | YES | Dynamic focus required | YES | YES | YES |
| Microscopy of specimens (High NA) | No external phase modulator | YES | Speckle | YES | YES | YES | YES |
| | Using an external phase modulator | YES | YES | YES | YES | YES | YES |

When imaging specimens and not the eye, due to the high numerical aperture (NA) that could possibly be achieved by bringing the tissue close to the microscope objective, the depth resolution in the confocal core of the OCT channel may become comparable or better than that of the OCT itself. Therefore, by applying AO. The depth resolution improves in the OCT channel as well, in comparison with low NA imaging, where the improvement is masked by the narrow OCT depth sectioning profile.

The table shows that in all circumstances, the confocal channel reports improvements of its parameters. Therefore, non-improvement of transversal resolution in the OCT without a phase modulator could be tolerated when a pair of OCT/confocal images is generated, where the morphology in transversal section is made visible in the confocal channel.

When the present disclosure is applied to microscopy imaging, even if the OCT channel does not show improvements in its depth resolution, an OCT channel is useful in addition to a confocal channel for the higher sensitivity of OCT. It is known that for skin systems, OCT could achieve at least double penetration depth. Therefore, there is still scope to combine the two channels, OCT and confocal, which by aberration control using AO as described in the present disclosure, could achieve an enhanced penetration depth.

No conventional systems are capable of producing high resolution images in both regimes, OCT and confocal. None are capable of producing B-scan images in both regimes, OCT and confocal. None are capable of producing C-scan images in both regimes, confocal and OCT. The Herman's and Zhang's papers mentioned above reported enhancement of the signal to noise ratio and of the signal strength when AO feedback was closed The Roorda and Zhang papers have shown improvement in the transverse resolution as well. However, none refer to OCT T-scan nor to OCT C-scans obtained based on the flying spot concept. WO 2003/105678 to C-scan OCT, but this operates on the full field principle (or coherence radar), of less sensitivity, and Zhang's OE paper refers to improved C-scan in the fundus camera regime (using a 2D CCD, which is well below the depth resolution of a confocal aperture).

In the embodiment in FIG. 1, the line in the raster image is determined by fast transversal scanning, i.e. by using one of the scanners only to generate a horizontal line or a vertical line over the object, or both to generate any profiles, such as ovals or circles, according to conventional scanning principles for handling a 2D scanner head. The 1D reflectivity profiles obtained this way are T-scans, which are generated in both channels, OCT and confocal. The configuration in FIG. 1 ensures pixel to pixel correspondence between the pixels in the two T-scans. T-scanning ensures:

1. An easy switch from B-scan to C-scan regime and
2. Less cross-talk between transverse pixels than a full field with flood illumination set-up.

None of the documents mentioned above on combination of imaging principles with AO have generated T-scans, therefore could not take advantage of points 1 and 2.

When closing the loop in the AO channel, the depth of focus shrinks due to improvement in the depth resolution of the confocal channel at the core of the OCT configuration. This affects the strengths of both T-scans, as explained below and opens several scanning strategies not contemplated by conventional imaging systems equipped with AO, nor conventional imaging systems alone, strategies allowed by the combination of focus scanning in the confocal channel with the coherence gate scanning in the OCT channel.

Focus Improvement Under AO Correction and Consequences.

1. Narrowing of the Confocal Sectioning Profile in the OCT Channel

When the AO channel compensates for aberrations, the axial resolution narrows to the level expected for an ideal focusing element in front of the object being imaged. This raises the problem of signal strength from depths outside the axial sampling profile of the confocal receiver at the core of the OCT channel. When imaging the retina, due to aberrations, the confocal core is known to have a depth sectioning profile not better than 300 µm. By applying AO, an axial profile as narrow as 50 µm could be achieved, which is an interval smaller than the retina thickness. Consequently, the improvement of the axial resolution due to AO leads to a reduction of signal for depths outside the confocal profile. Therefore, depth of focus shrinkage requires control of the focus in the OCT channel and open the perspective of generating B-scan images in the confocal channel as explained below.

2. Focus Position in AO Versus the Desired Focus Position in OCT and Confocal Channels The AO channel may dictate a shift in the focusing towards the depth where the maximum signal originates from. For instance, when imaging the eye, a layer of highest reflectivity, such as the retinal pigment epithelium (RPE) determines the closed loop AO channel to focus at the depth where the RPE is. Consequently, there are two effects, due to AO, narrowing of the axial sampling profile and shift of such peak towards the depth dictated by the AO channel.

Dynamic focus procedure comprises moving the focus depth in the confocal core of the OCT in synchronism with the coherence gate, and in this way selecting signal in the OCT from that depth where the two optical paths, in the object and reference paths are matched. This is possible by controlling the following element 5 and the translation stage 112 in synchronism by signals 5c and 112c sent by the controlling PC 4. However, in an OCT system equipped with dynamic focus, with the function of aberration compensations active in the AO, it is difficult to predict the operation of the dynamic focus. When the convergence of the beam is altered by actuating the focusing element, the corrector 22 tries to compensate this change in convergence and counteracts its effect by curving the corrector 22. Under closed AO loop, the AO system maintains the best focus at the depth of the RPE level while the dynamic focus tries to move the focus to different depths in synchronism with depth scanning as required for generation of B or C-scans.

Therefore, different solutions for addressing the conflict between the wavefront corrector and dynamic focus are required in order to maximise the strength of signal in both channels and even more, select the depth where such strength is maximum for diagnostic reasons.

3. Using Focusing Elements in the Common Path

Using the Corrector 22 Under Closed Loop Conditions 3.1. A bias correction could be applied to the signal sent by the wavefront sensor 23 to adjust the focus away from RPE, by changing the convergence of the corrector 22. Such a signal could be applied to the AO feedback loop 24, in the form of a bias, to implement depth focus scanning as required for B or C-scanning regime. Under perfect adjustment, the focus points of the lenslet array 23, are on their axes and coincide with a grid of points for aberrations zero. No correction signal is applied to the corrector 22. In the presence of aberrations, the focus points created by the lenslet array deviate from the grid points for aberrations zero. These deviations are read by the photo detector array 235 which are translated to controlling signals for the actuators of the corrector 22, to create a wavefront with opposite aberrations at the cornea and create a flat wavefront surface immediately after. Part of errors signals generated by the feedback loop 24 refer to focus correction, which controls the 22 to spherical curb. The error signal of the closed loop, which tells the loop where to stop correction, could be mismatched by applying bias signals. In that case, the loop will interpret distribution of focus points on the array 235 as points of null correction. While the maximum strength of the signal still comes from the RPE, under such bias signal, the corrector curves the beam to focus away from the RPE. In this case, the focus points of the lenslet array deviate from the regular grid corresponding to perfect correction and the CCD array 235 outputs signals corresponding to a defocus. However, the other aberrations are still compensated, if the bias signals represent only the aberration of defocus. In this way, focus correction can be applied with the AO loop closed.

By applying adjusting signals via the AO electronic feedback link to the wavefront corrector, the position in depth where both channels, confocal and OCT focus is changed. T-scans are collected from such new focus positions, which could be changed according to the depth scanning procedure controlled by the PC, 4, B or C scan, i.e. synchronous with depth scanning in the OCT channel, line 112c.

3.2. Using the Corrector 22 Under Open Loop Conditions

In this case, to avoid a conflict between the corrector 22 and the focusing element 5, the system operates under open AO loop, according to the following steps: (1) with no depth scanning, the AO system is used to evaluate and then correct for the aberrations in the at least correcting path, step which proceeds with no or with T-scanning present, (2) control signals towards the wavefront corrector are stored, (3) the link between the wavefront sensor 23 and the wavefront corrector 22 is interrupted and (4) focus adjusting signals are applied to the wavefront corrector 22, to modify the position in depth where both channels, confocal and OCT focus and T-scans are collected from, while the same correction of aberrations according to the stored values in step (2) is maintained.

3.3. Using the Wavefront Sensor 23 Under Closed Loop Conditions

Another focusing modality could be implemented by altering the distance between the lenslet array 231 and the photodetector array 235. By moving the lenslet array 231 towards the photo detector array 235, points behind the RPE, i.e. deeper will be focused on the photodetector array 235 and the array 235 will supply the same aberration information as before plus a defocus information. This will determine a different curvature of the corrector 22 to focus the object beam back on the RPE. In doing so, the corrector 22 will now focus the OCT and confocal beams at points in front of the RPE.

Similarly, by moving the lenslet array 231 away from the photodetector array 235, the corrector 22 will bring the RPE in focus and by doing so, the corrector 22 will now focus the OCT and confocal beams at points behind the RPE. This type of focus is compatible with closed loop correction to correct the aberrations other than focus and scan in depth in the confocal channel and in the confocal core of the OCT system.

3.4. Using the Curvature of the Beam Generating the Reference Point for Aberration Evaluation Another focus method that embodiments of the invention could use introduces defocus into the wavefront sensing beam. The embodiment in FIG. 1 does not allow such an approach, as the same source, 11 is employed for imaging as well as for the AO system. This method will be described in conjunction with the embodiments discussed in relation to in FIGS. 3 to 7.

3.5. Using the Focus Element 5 Under Open Loop Conditions

Focus for both OCT and confocal channels can be shifted away from that of the wavefront sensor 23 using the focusing element 5. Focus is changed by moving the translation stage 5a, which supports the two mirrors 55 and 56. In this case, to avoid a conflict between the corrector 22 and the focusing element 5, the system operates under open AO loop, according to the same steps as before.

3.6. Using Focus Elements in the Uncommon Path

The wavefront sensor receives most of the light from the bright scatterers at the level of the retinal pigment epithelium (RPE) layer and determines the corrector to focus at the same depth. The focusing elements 115 (in the uncommon OCT path) and 122 (in the uncommon confocal path) are adjusted for the best focus of the OCT channel and confocal receiver channel respectively using a non-aberrated object. Then, when the system is directed to the eye, both channels will focus at the depth where the wavefront sensor 23 selects maximum intensity, i.e. at the RPE. Then, actuating on the elements 115 and 122, the focus in the two channels can be adjusted at different depth positions. They could be adjusted at the same depth but different from that of the wavefront sensor, or at two different depths to allow independent adjustment of the imaging depth in the OCT system and the confocal system. Alternatively, it is also possible to use a combination of focus adjustment 5, with that of elements 115 and 122 to reduce the amount of adjustment applied on the corrector 22, which will reduce the dynamic range of correction. Alternatively, instead of controlling two focusing elements 115 and 122, only one focusing element in the uncommon 2-path, placed between splitters 31 and 32 could be used.

It should be apparent to those skilled in the art that the methods above could be combined to extend the focusing range or modify the start depth and end depth of the two depth ranges in the OCT and confocal channel. For instance, controlling the corrector or moving the lenslet array 231 which act on both channels could be combined with methods which change focusing in one channel only.

Furthermore, the improvements in focusing obtained by using the corrector 22, the wavefront sensor 23, focusing element 5, focusing elements 115 (for the OCT channel) and focusing element 122 (for the confocal channel) could provide advantages in scanning for single channel systems, whether the system is implemented as either OCT or confocal systems.

Focus adjustment is very important in the process of dynamic focus, which means maintaining the confocal gate in the confocal system at the core of the OCT channel in synchronism with the coherence gate. By changing the optical path difference in the OCT channel, for instance by using the translation stage in via the line 112c, the coherence gate is placed at different depth or moved through depth of the object 8, and scanning in depth is performed to generate B-scans and acquire C-scans from different selected depth positions. Because under the AO regime, the coherence gate could be as narrow as 50 μm, it is important to ensure a dynamic focus procedure to achieve maximum sensitivity in the OCT channel. Any of the possibilities explained above or a combination of such possibilities could be applied, to extend the focus range or to make it different from that in the confocal channel.

B-scanning Regime

Several T-scans are acquired for different depths either by altering the depth in steps or by changing it continuously at a much slower pace than that of T-scanning, to generate T-scans from essential the same depth. In this way, (x,z), or (y,z) images, with z along the optic axis could be generated. By actuating on both transverse scanners to generate an oval profiled T-scan, cylindrical images could be equally generated.

OCT channel: A B-scan is obtained by changing the optical path difference in the interferometer, by actuating on the optical path difference between the object path length and reference path length, by acting on stage 112 via control line 112c. This could be obtained with or without dynamic focus procedure explained above. In case dynamic focus is applied, then controlling signal via one or a combination of lines 24c, 231c, 5c, or 115c are sent synchronously with control signal 112c.

Confocal Channel:

A B-scan is obtained by changing the focus control line, using one or a combination of the possibilities mentioned above, by actuating on the 24c, 231c, 5c, or 122c.

Pairs of OCT and Confocal B-Scans

Pairs of B-scan OCT and confocal images have been obtained as described in WO03086181A1. FIG. 8 in this application shows such a pair, where due to the large depth of focus (due to aberrations left uncompensated) in the confocal channel, the B-scan confocal image does not provide any depth information, and therefore, all T-scans, at different depths are the same. The embodiment in FIG. 1 allows generation of a meaningful confocal image due to the much improved resolution depth. Such a pair of images display images which could provide diagnosis value not available by examining the OCT or the confocal B-scan image alone. Generally, the OCT image will display the maximum depth resolution in the pair when imaging the eye, while the confocal image will display a less speckled image than in the OCT image, speckle which masks less the improved transversal resolution along the T-scans in the image. The OCT image and confocal image should display a lateral transverse resolution of less than 3 microns, sufficient to observe photoreceptors and tiny vessels in the retina. However, due to the interference principle, speckle will affect the OCT image but less the confocal image, therefore simultaneous presentation will provide the user insights into the intimate structure of the tissue not possible by interpreting the OCT or confocal image alone.

A depth resolution in the confocal image of 50-100 microns is sufficient to observe large vessels as well as for profile measurements of the foveal pit and optic nerve. Such measurements, of the optic nerve cup and other spatial parameters are essential in diagnosis of glaucoma. Depth resolution of sub-micron is achievable in the OCT channel of the retina by using a sufficient large band optical source 11.

Therefore, if sufficient information along the T-scan is obtainable from the confocal B-scan, due to AO improved transverse resolution, it may not be necessary to introduce external phase modulation in the OCT channel, according to comments on the influence of the type of phase modulation employed on the transverse resolution in the OCT channel above.

In producing such improved resolution pairs of images under AO control, several focus procedures are possible, as derived from the presentation of different focus alternatives above.

C-scan Regime

Several T-scans are acquired for different values of the rectangular transverse coordinate either by altering the frame scanner in steps or by changing it continuously at a much slower pace than that of T-scanning, to generate T-scans from essential the same rectangular transverse coordinate.

OCT Channel:

A C-scan from a given depth is obtained by controlling the two transverse scanners 61 and 62 while maintaining the optical path difference in the interferometer constant. By changing the optical path difference, a C-scan from a different depth is obtained and in this way, stacks of OCT C-scan images can be obtained. This could be done with or without dynamic focus procedure explained above. In case dynamic focus is applied, then controlling signal via one or a combination of lines 24c, 231 c, 5c, or 115c are sent synchronously with control signal 112c. The depth change can also be applied continuously at a pace slower than the frame scanner.

Confocal Channel:

A C-scan is obtained from a given focus, by controlling the two transverse scanners 61 and 62 while maintaining the same focus. By changing the focus, a C-scan from a different depth is obtained and in this way, stacks of confocal C-scan images. This could be obtained using or a combination of the possibilities mentioned above, by actuating on the 24c, 231c, 5c, or 122c. The depth change can also be applied continuously at a pace slower than the frame scanner.

Figure 2A:
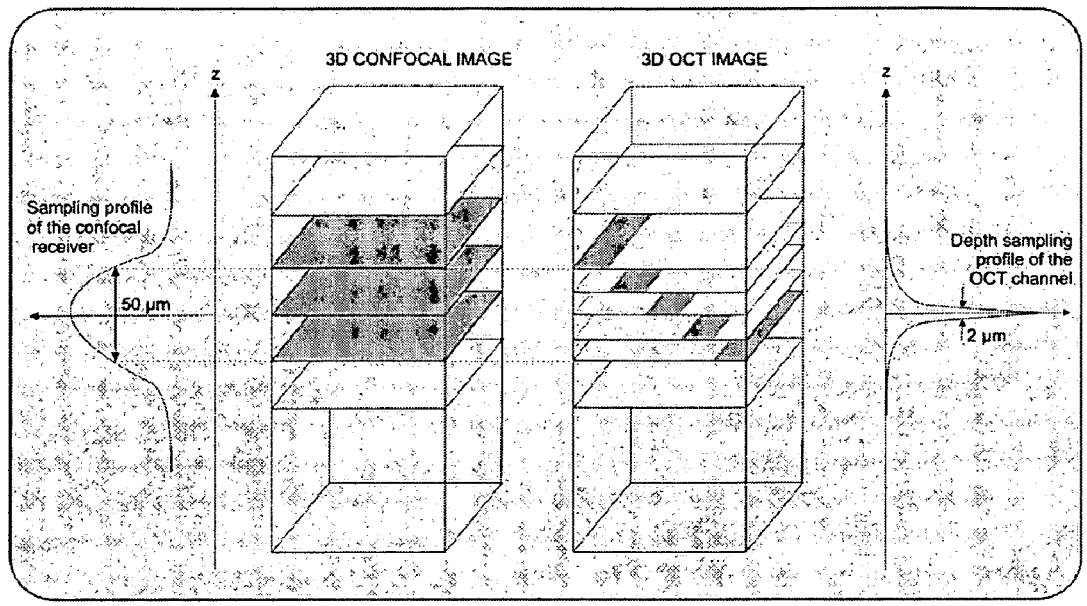
FIGS. 2a and 2b shows two strategies in collecting depth resolved C-scan pairs.

Pairs of OCT and confocal C-scans have been reported by using one of the embodiments in U.S. Pat. No. 5,975,697 and U.S. Pat. No. 6,769,769 patents. However, stacks of such pairs collected with the methods described in these two patents show anunchanged confocal image, due to the very large depth of focus in the aberrated confocal channel. The C-scan confocal image in the pair does not provide any depth information, and therefore, all C-scans, at different depths are the same. The embodiment in FIG. 1 allows generation of a more meaningful confocal image due to the much improved resolution depth. Such a pair of images provide diagnosis value not available by examining the OCT or the confocal C-scan image alone. This strategy, of collecting pairs of depth resolved C-scan images in both channels, allowed by AO aberration correction, is illustrated in FIG. 2a, where the confocal image in the pair is scanned in synchronism with the OCT image.

The OCT image will be the thinnest in the pair, while the confocal image will display a less speckled C-scan image than the OCT image, speckle which masks less the improved transversal resolution along the T-scans in the image.( )

Depth Guidance of C-scan OCT Images Via a Fixed Depth Confocal C-scan Image

Figure 2B:
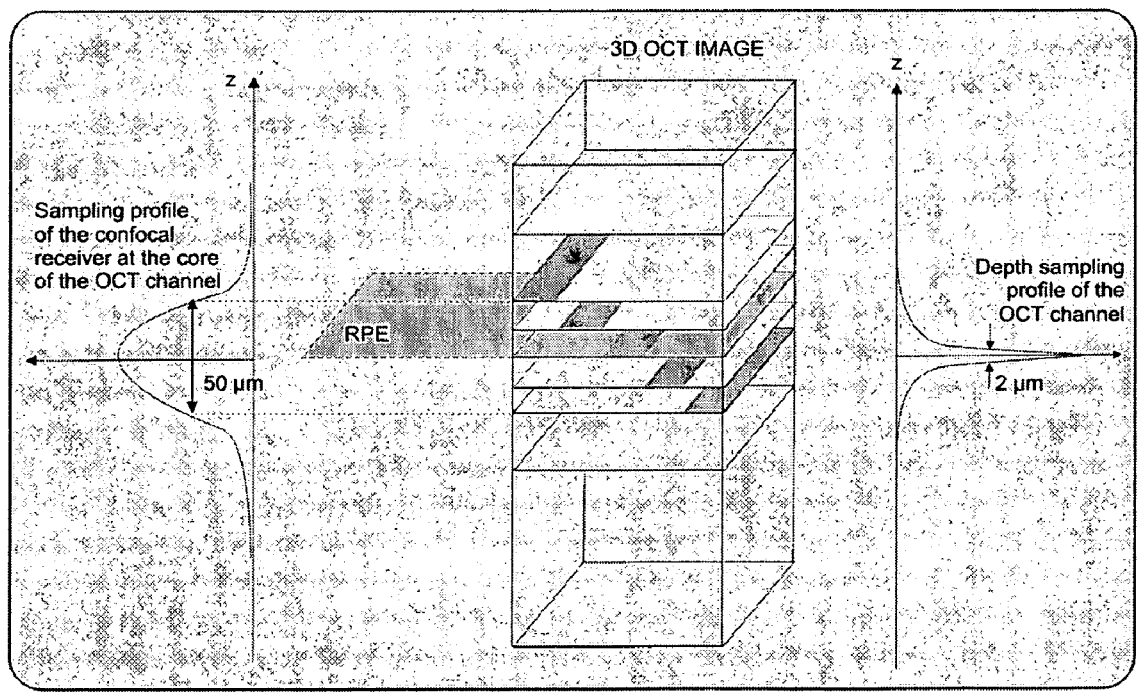

In C-scan regime, it may be advantageous not to produce stacks of confocal C-scan images, but to provide guidance in collection and interpretation of C-scan OCT images from different depths. Due to much enhanced depth resolution in the confocal channel when applying AO correction, better selection in depth is possible. In conjunction with independent focus adjustment in the confocal channel as explained above, for instance by actuating in the non common path, via 122c, on the lens 122 in the uncommon confocal path, allows fixing the depth of the confocal C-scan image. This strategy, allowed by AO aberration correction, is illustrated in FIG. 2b. This could be left at the depth selected by the AO channel, usually at the RPE level as shown in FIG. 2b, or could be independently set at other depth position, depending on the user choice investigating the pathology, either in the choroid, below the RPE, or above the RPE, at the level of the retinal nerve fibre layer. Such guidance was not possible in conventional combined OCT/confocal instruments, where the confocal image had usually a low depth resolution C-scan image, close to that of a fundus camera, i.e an image where the brightness of each pixel in the raster was given by an integration over 300-500 microns in depth. Such low resolution did not allow separation between choroid and the fiber layer, which are apart by approximately 500 microns.

Sequential OCT/Confocal with AO Correction

In the embodiment in FIG. 1, the OCT and confocal channels can operate simultaneously to produce pairs of OCT and confocal images at the same time. Alternatively, the confocal channel 12 and splitter 32 could be eliminated and the core of the OCT system could be sequentially used, as disclosed in the application US20040233457A1 to generate an equivalent SLO image. The switch between the confocal and the OCT regime can be implemented by using an opaque screen to block the reference beam, shown in dashed line, 116, where the two photodetectors 106 and 107 are APDs. Their gain is self adjusted depending on the incident power, low in the OCT regime due to the high power from the reference beam and high in the confocal regime, when the only power is that from the object. Such embodiments have the advantage of being less complex and that more signal returned from object 8 is used in each channel, OCT or confocal than being shared by the two channels via the beam-splitter 32.

In this case, a confocal B-scan image is obtained after the blocking screen 116 is in place, by scanning the focus based on one of the procedures described for focus adjustment in the confocal channel at the core of the OCT channel. Similarly, C-scans at different depths in the confocal channel are obtained via the same focus procedures after the screen 116 is in place.

OCT B-scan and C-scan images can be obtained for the case of simultaneous OCT/confocal imaging.

In comparison with sequential OCT/confocal images obtained with conventional systems via non-corrected aberrated paths, the images collected with the embodiment in FIG. 1 have better signal to noise ratio. Alternatively, because the signal strength is enhanced due to correction of aberrations, less power could be sent to the eye to obtain similar signal to noise ratio as that in images generated via aberrated paths.

In a different aspect, embodiments of the invention provide solutions for imaging with high resolution in an OCT and fluorescence confocal channel by compensating the aberrations using an AO closed loop channel. By suitably combining dichroic beam-splitters with the excitation wavelength, different possibilities exist. Illustrated here is an example of how to reconfigure the embodiment in FIG. 1 to excite and image the indocyanine green (ICG) fluorescence in the eye. The source 11 could be chosen as a superluminiscent diode operating at 793 nm and the beamsplitter 32 could be a hot mirror which transfers (reflects as an example in FIG. 1) the fluorescence, which peaks at 835 nm towards the confocal receiver 12. A supplementary filter, 124, shown in dashed line in FIG. 1, could be provided to eliminate the excitation wavelength at 793 nm and enhance the contrast, as presented in the U.S. Pat. No. 6,769,769. Filter 124 could be a long pass filter, and could be mechanically inserted or pulled out, customising the channel on either the fluorescence or on the excitation wavelength, residually reflected by the dichroic splitter 32. This leads to a system with 3 channels, OCT, confocal and fluorescence.

By using another dichroic splitter in the output path towards the confocal channel 12, to spectrally separate the excitation light from the fluorescence light, a confocal channel on the excitation wavelength and a confocal channel on the fluorescence could operate simultaneously and not sequentially. In this case, 4 is equipped with a three channel simultaneous display system.

The AO system corrects for aberrations and in this way, high resolution is achieved in the OCT channel at 793 nm and in the fluorescence channel at 835 nm. Such a system could be valuable in distinguishing very small vessels in the retina flown by the ICG, with potential diagnostic in age related macula degeneration and choroidal neovascularisation.

Single Path and Double Path Aberration Correction

A further possibility for the embodiment in FIG. 1 is for the AO system to operate in single path correction. Wavefront correction could be introduced in single and double path configurations. One can use correction in single path when the corrector operates on the beam emerging from the object but not on the beam going to the object. In such systems, the beam still suffers the aberration while propagating to the object through the imaging focusing element, such as the eye lens. By using a very thin beam towards the eye pupil, aberrations are kept low because the beam is sent via the centre of the eye. The larger the beam diameter, the better the resolution. Therefore, for the returned beam, the eye pupil is kept large, 5-7 mm, in which case the beam cumulates aberrations and by correcting for these aberrations, transverse and depth resolutions corresponding to the large beam diameter value are possible to be achieved. In double path, the corrector 22 responds to aberration introduced in the beam while propagating to the retina as well as to the aberration cumulated in the return path of the beam, in which case the beam diameter is generally the same for the incident and for the emerging beam. The single pass correction has advantages in terms of less aberrations to be collected and corrected for.

The embodiment in FIG. 1 can be used single pass, by restricting the object beam diameter out of 110, by using a short focal length focusing element 110. In this way, confocal channel and OCT channel operate under single path aberration correction.

When the confocal channel 12 is tuned on the fluorescence generated in the object, 8, by beam of source 11, single pass correction is applied to corrector 22 for both OCT object beam and fluorescence beam. Because the wavefront sensor 23 operates on the wavelength of source 11, in FIG. 1, the interface optics elements should preferably be mirrors.

Those skilled in the art will recognise that other possibilities exist in terms of customising the beam-splitters in FIG. 1, without diverting from the scope of the invention, to achieve similar functionality on different other pairs of excitation and fluorescence wavelengths, to address imaging of other fluorescent drugs for the eye or confocal microscopy.

Figure 3:
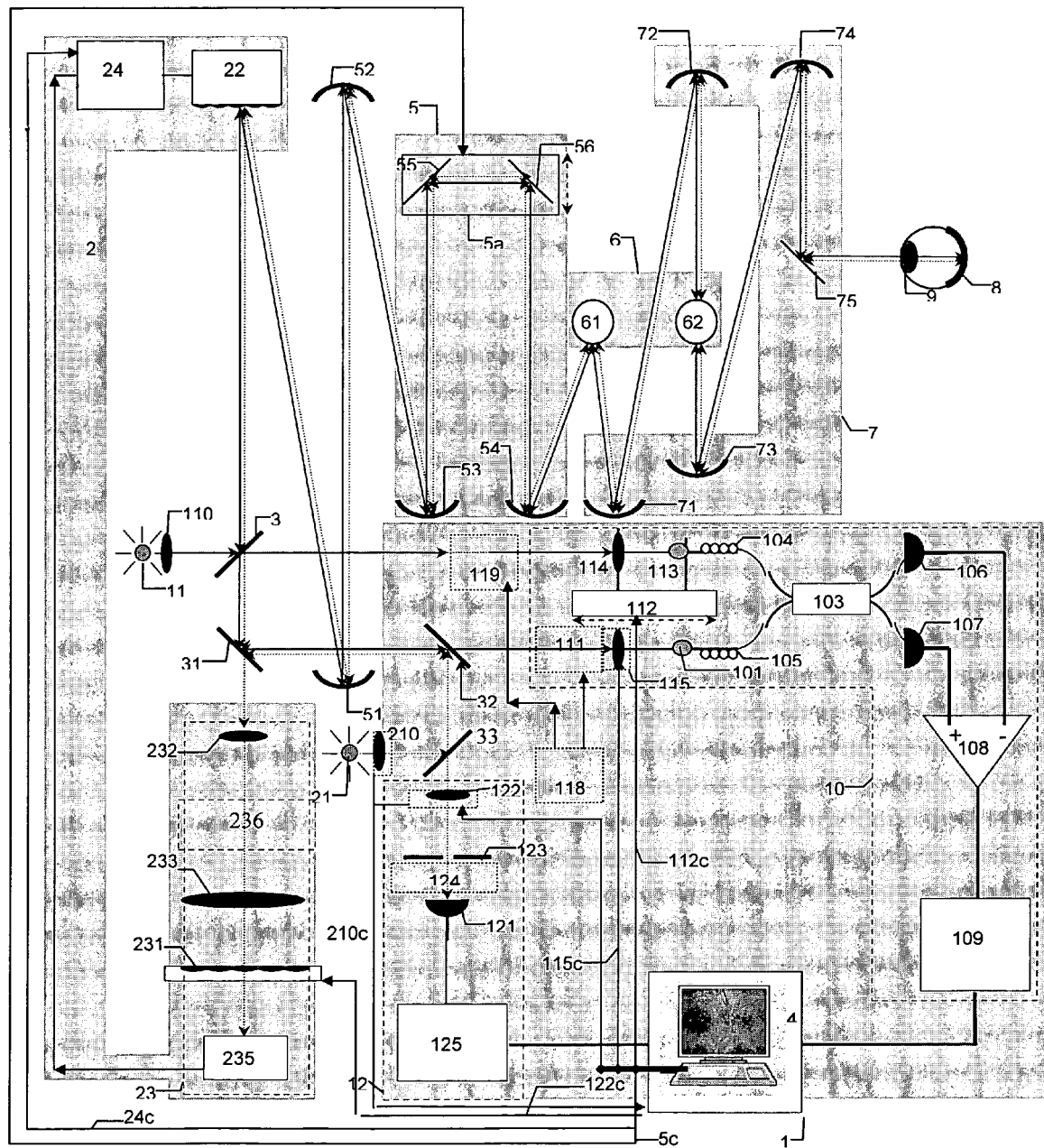
FIGS. 3 and 3a show two versions of a second embodiment of the system for high resolution imaging of an object via an aberrated path.

FIG. 3 shows a second embodiment of the invention, where the confocal channel 12 and the AO system 23 use a different source 21 to that used by the OCT channel. Features of the second embodiment that are the same as those in the first embodiment will not be discussed.

Light from source 21 is collimated by the focusing element 210. The two systems (i.e. OCT and confocal) operate at different wavelengths. For instance, for imaging the retina, the preferred wavelength is in the 700-1100 nm range. This embodiment is especially useful for an OCT channel for skin, where the source 11 operates at 1300 nm for better penetration depth in the OCT channel than at 800 nm (scattering in tissue is less at 1300 nm than at 800 nm). However, at this wavelength, avalanche photodiodes (APD) and photo-multipliers have low gain and the wavefront corrector and confocal channel may not achieve the same sensitivity as in the embodiment in FIG. 1. Therefore, in order to use Silicon APDs, the wavelength of the source 21 is chosen in visible or infrared such as 800 nm. In this case, the beam-splitter 33 used to inject light from source 21 into the common path is dichroic, beamsplitter 32 is also dichroic, for instance a cold mirror, to allow 1300 nm through and reflect 800 nm. In this way, less OCT signal is lost than in the embodiment in FIG. 1. In such an embodiment, OCT operates at a wavelength of 1300 nm, while the confocal receiver and the wavefront sensor in the AO channel operate at a different wavelength, 800 nm. Light from 21 is sent towards 32 along the confocal uncommon path, then to uncommon 2-path to 31, to the common path up to the object. Light returned from object 8, if of wavelength of the source 21 will be reflected by 32 towards 12 and if of wavelength of source 11 will reach 101. Light of both wavelengths reach the wavefront sensor 23, therefore splitter 31 is a neutral splitter. In this case, the AO system can be customised on the OCT wavelength, of source 11. If the wavelength is 1300 nm, photodetector array 235 is an InGaAs array.

As a different functionality, source 21 can be used to provide the wavefront sensing beam only. For instance, 21 could be a visible source, or 670-800 nm and source 11 operates at 850 nm. In this case, the confocal and OCT channel operates at the same wavelength, 850 nm, which for analysing of tissue could be 1300 nm and the photodetector 121 in the confocal channel 12 uses a Germanium APD.

As another possibility provided by such embodiments, involves using a spectral filter 236 in front of the wavefront sensor 23, using either the wavelength of source 11 or 21 can be chosen to serve as wavefront sensing beam. In this case both wavelengths should fit within the spectral sensitivity of the photodetector array used, Silicon or InGaAs. For instance, for the eye imaging source 21 could operate at 670-800 nm and the OCT at 820-920 nm.

In terms of the focusing possibilities allowed by the embodiment in FIG. 1, all are possible here too. However, in this case if a focusing element is used in the uncommon 2-path, its utilisation will separate in depth the confocal depth selection from that of the confocal core of the OCT channel.

In addition to the focusing alternatives compatible with the embodiment in FIG. 1, this embodiment allows a supplementary solution, opened by using the curvature of the beam generating the reference point for aberration evaluation. The embodiment in FIG. 1 does not allow such an approach, as the same source, 11 is employed for imaging as well as for the AO system. In the embodiment in FIG. 3, another novel possibility is created if the source 21 is also used to generate the wavefront sensing beam. By moving the focusing element 210 which respect to source 21, the convergence of the wavefront sensing beam is changed and the beam will focus in front or behind the RPE. In such circumstances, the wavefront sensor 23 will detect a defocus and actuate on the corrector 22 to focus the wavefront sensing beam back at the RPE depth. In doing so, the convergence of the confocal and OCT beam will also change, resulting in the OCT fibre input 101 and pinhole or fibre input 123 being conjugate with points other than the RPE. To generate the depth focus scanning as required by B and C-scanning regimes, the relative position of the focusing element 210 to source 21 could be changed under control line 210c. Consider that 210 was moved closer to source 21. In that case, the wavefront sensing beam will focus behind the RPE, the corrector will be actuated to bring it back to the RPE and the confocal channel and the OCT channel will consequently focus at a point in front of the RPE. Similarly, by increasing the distance between source 21 and focusing element 210, the OCT and confocal channel will be focused at points behind the RPE. It will be clear that, the method operates in closed loop.

It should be obvious for those skilled in the art that this method could be combined with any other method of focusing presented in connection with the embodiment in FIG. 1., to extend the focusing range or modify the start depth and end depth of the two depth ranges in the OCT and confocal channel.

Figure 3A:
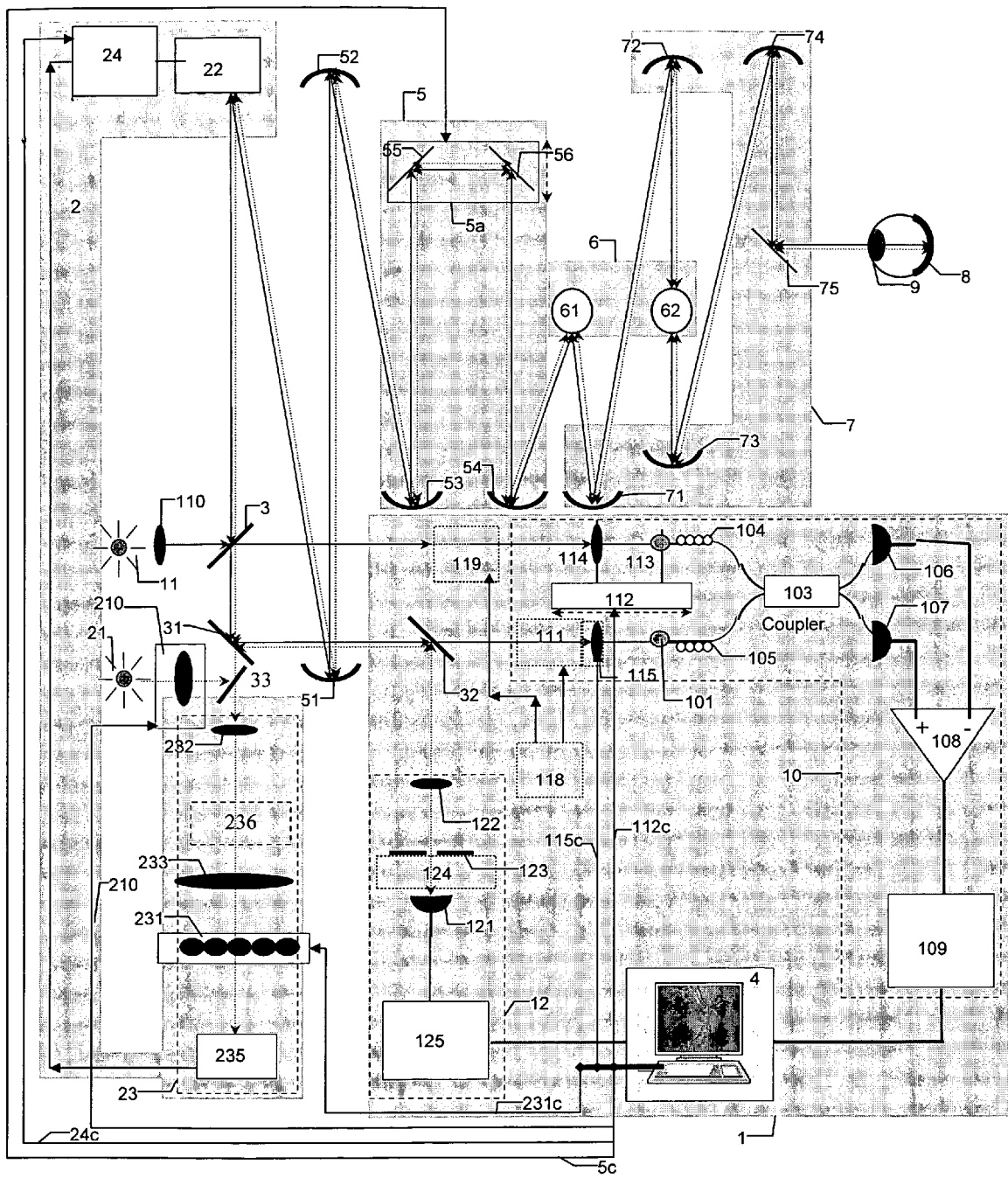

A version of the embodiment in FIG. 3 is shown in FIG. 3a. The beam-splitter 33 is incorporated in line with the wavefront sensor, 23, after beam-splitter 31, in which case the beam-splitter 31 could be dichroic. Light from source 21 is launched into the common path and if splitter 31 is dichroic, only light of the same wavelength will reach the wavefront sensor 23. In this case, it is possible for the OCT and confocal channel to operate on the same wavelength and for the wavefront sensor to operate on a different wavelength, of the source 21. In this case the splitter 32 is neutral. Similar to the embodiment in FIG. 3, the confocal channel could be tuned at the same wavelength as that of source 21, in which case 31 is neutral and 32 is dichroic. Such an example is for imaging of skin, where source 11 operates at 1300 nm, and as explained above, by using Silicon based CCD array in 235 and Silicon APD in 121, higher sensitivity is achievable than that when operating at 1300 nm.

It may also be possible, that source 21 serves the confocal channel only, in which case apart from splitter 33, splitter 32 would also be dichroic.

Splitter 33 could be placed between OCT splitter 3 and splitter 31, but this path is shared by both confocal and OCT paths and any splitter here will introduce losses in both channels.

The source 21 to be used in FIGS. 3 and 3a could be low coherence or lasers, while the source 11 could be a low coherence source.

Figure 4:
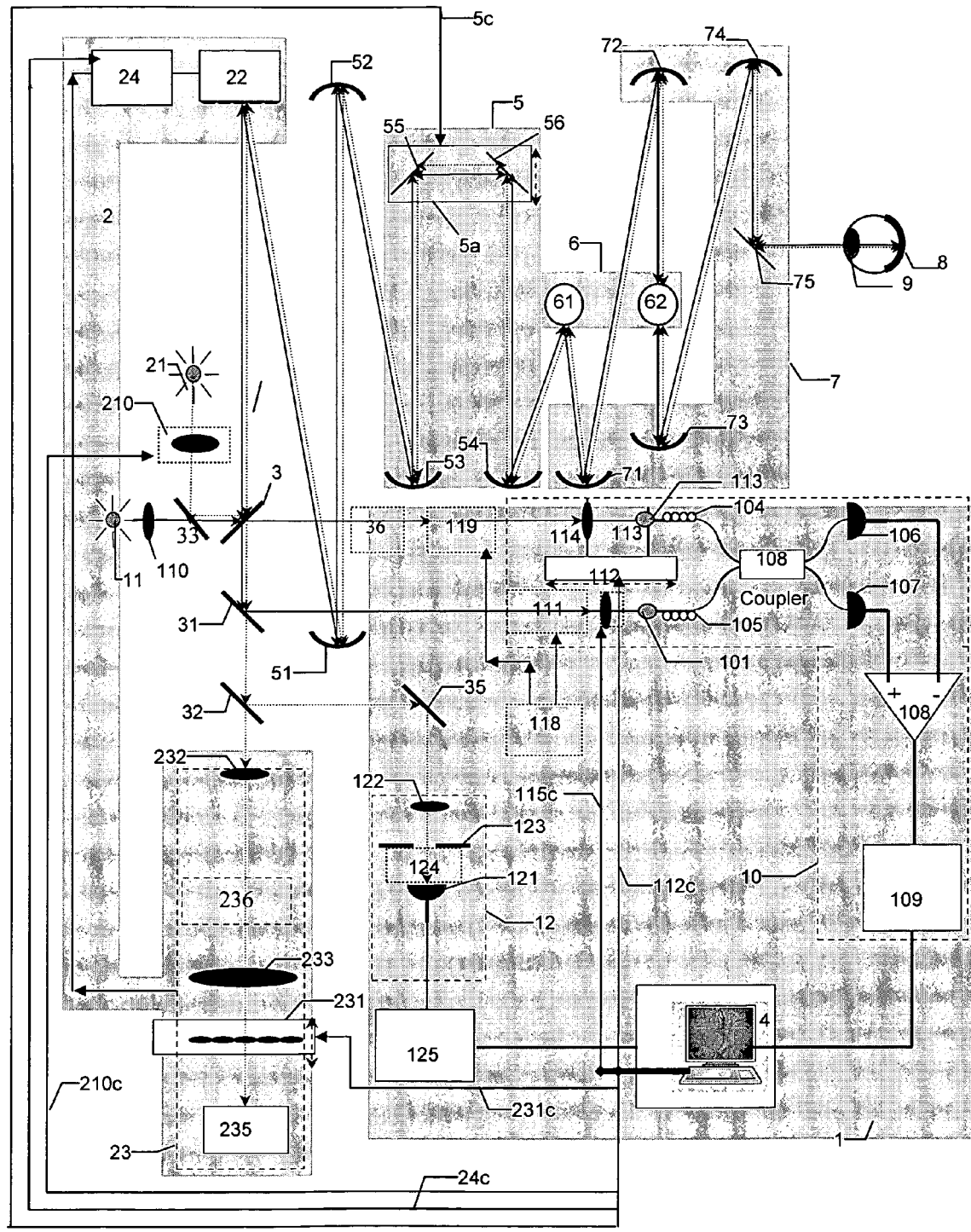
FIG. 4 shows a third embodiment of the system for high resolution imaging of an object via an aberrated path

A different solution is shown in the embodiment in FIG. 4 to minimise the losses in the OCT channel. In this case, the source 21 delivers the wavefront sensing beam. The beam from the source 21 is introduced in the common path via a neutral or dichroic splitter 33, and via the OCT splitter 3. To stop light from 21 reaching the reference input fibre 102, blocking filter 36 is used to reject light of the frequency of the source 21. This is feasible especially when the wavelength of the two sources are different and easier if the source 21 is a laser. Rejection of light is easier if the band to be rejected is narrow instead of wide band.

Consider that the wavelength of source 11 is 850 nm and the wavefront source 21 operates at 670 nm. All the signal at the OCT source wavelength returned from the object 8 is sent towards the object input fibre 101 of the OCT channel by using a dichroic beam-splitter 31, to reflect the OCT wavelength, e.g. 850 nm, and transmit the wavelength from source 21 (670 nm). At the other output of the beam-splitter 31, the beam of wavelength of the source 21 is sent towards the wavefront sensor 23 and confocal receiver 12 via a beamsplitter 32, with element 35 being a mirror. The splitting ratio of the splitter 32 is chosen depending on the sensitivity of the confocal channel 12 and the wavefront sensor 23.

In the embodiments described in relation to FIGS. 3, 3a and 4, the corrector 22 is used by both wavelengths, of the two sources, 21 and 11 to offer a reduced aberration beam to the confocal channel and OCT channel operating at different wavelengths. Therefore, optical elements in the paths traversed by both wavelengths have to be achromatic, therefore mirrors are preferably used in the interface optics 7 and focusing element 5.

Single and Dual Path Correction in the Same Set-up

Further functionality is achieved if the two beams emergent from the two sources, 11 and 21 have different beam diameters. In the spirit of single path correction as explained in connection with the embodiment of FIG. 1 above, essential is to launch an object beam sufficiently thin for the aberration in the launching path to be neglected. Consider that focusing element 110 is of long focal length, so source 11 generates the wavefront sensing beam for dual path and the focusing element 210 is of short focal length, so source 21 generates the wavefront sensing beam for single path correction.

Sources of Different Wavelength

Using sources with sufficient separated wavelengths, a band pass filter 236 could be provided in the wavefront sensor 23 to select between single path and dual path.

Similar Spectra Sources

The two sources (source 11 and source 21) could be two similar low coherence sources operating at similar wavelength values with similar optical bandwidth. In this case, the selection single path or dual path is obtained by switching on and off one or the other optical source. A blocking filter, 36, would not therefore be necessary.

Figure 5:
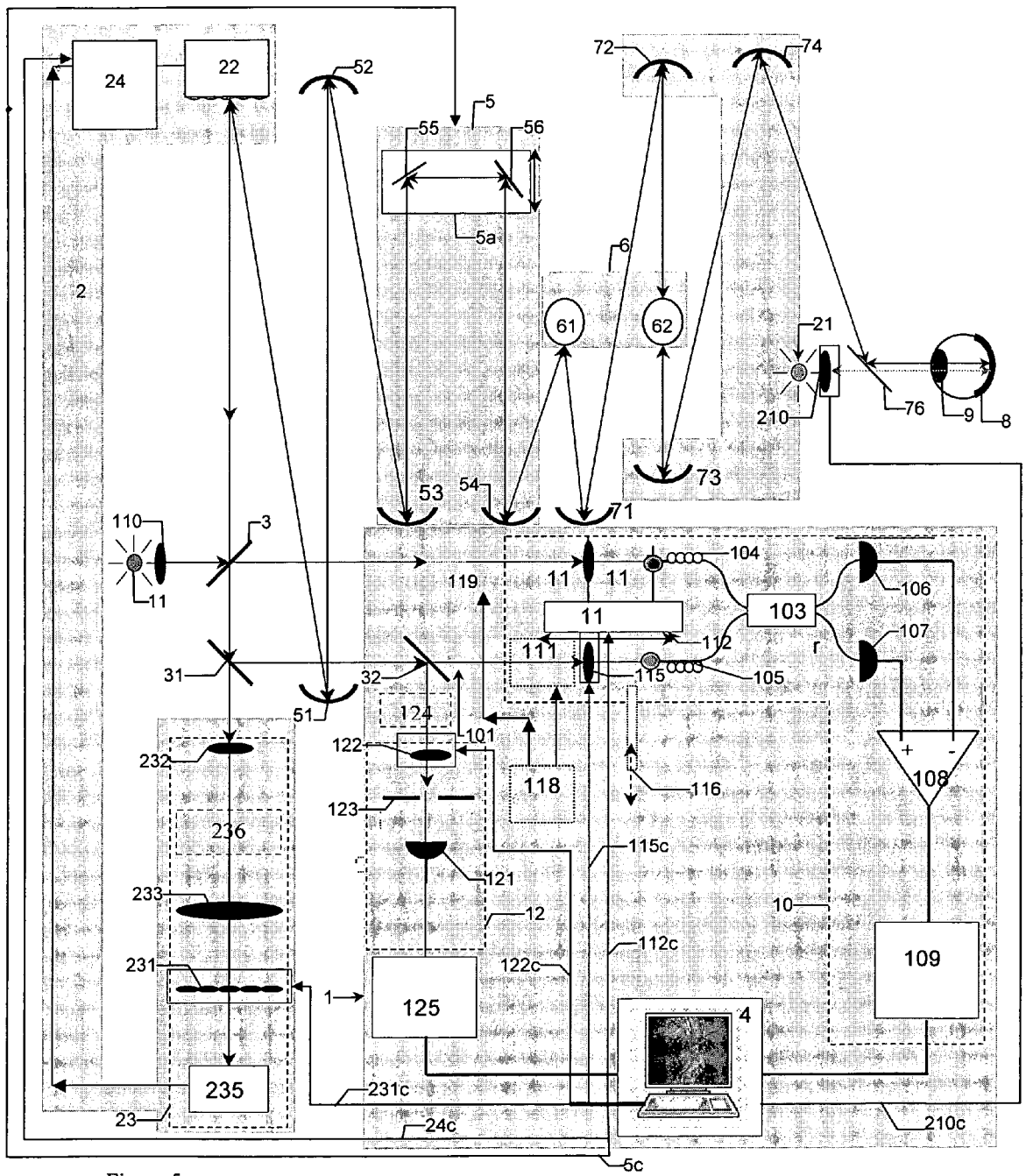
FIG. 5 shows a fourth embodiment of the system for high resolution imaging of an object via an aberrated path

FIG. 5 shows another embodiment of the system for high resolution imaging, where the correction of aberrations is applied in single path. A source 21 is provided to send light via a focusing element 210, through a beamsplitter 76, which creates a reference spot on the object, retina 8 in FIG. 5, to be used by the wavefront corrector 23. To reduce losses on the splitter 76, its splitting ratio can be optimised to allow most of the beam from the common path pass towards and from the object, 80-98%, and this could be achieved by using a sufficient power source 21. The beam out of source 11 can be also prepared thin by using a short focal length focusing element 110, such as a short focal length lens or a high power microscope objective or very curved spherical mirror. For instance, for the eye, a thin beam could be considered when in the range of 0.5 to 1 mm. In this way, the aberrations incurred when the beam from 11 passes through the imaging focusing element 9 can be ignored. In this case, aberrations are incurred by the two beams, of the source 11 and 21 when light backscattered from the object 8 traverses the imaging element 9 only. Because scattering is of wide angle, both beams gain the diameter of the imaging focusing lens 9, the pupil in case of the eye. Therefore, the wavefront sensor 23 practically senses single path aberrations and the wavefront corrector 22 is driven to minimise the aberrations for the wavefront sensing beam generated by the source 2 in return from the object 8 along the common path. By doing so, single pass aberrations for the beam of the source 11 are also compensated for.

Different Regimes of Operation

Single Path Correction, Single Orientation Axis Correction Via Lenses, Open Loop Source 21 could be a laser or a low coherence source of different wavelength than that of the source 11. The wavefront sensor 23 could be set to work on the wavelength of source 11 or source 21, by using a band pass filter 236, in front of the wavefront corrector 23 to select the desired wavelength band. When the wavefront sensor 23 works on the beam of source 21, it is possible to use lenses instead of mirrors in the interface optics between the object 8 and the corrector 22. In other words, all elements 51 to 54 and 71 to 74 could be lenses, whereby using a blocking filter 236 in the wavefront sensor 23, the reflections of the beam from source 11 by lenses will not reach the photodetector array 235 in the wavefront sensor 23. Lenses are of lower cost and introduce less aberrations than mirrors when utilised on axis. To further reduce losses in the OCT and confocal channels, beamsplitter 31 could be dichroic, allowing most of the light from 11 to pass towards the OCT fibre input 101 and confocal receiver and most of the light of 21 to pass towards the wavefront sensor 23. However, to collect the aberrations, the scanners 61 and 62 have to be set at an angle to route the object beam along the wavefront sensing beam, usually on-axis. At any other angle, the wavefront sensor is deprived from the wavefront sensing beam generated by the source 21. Therefore such an AO system can only operate in open loop when using source

21, according to the following steps: (1) with no depth scanning and no T-scanning, i.e. with the scanners 61 and 62 fixed on tilts to direct the object beam along the direction of the wavefront sensing beam, the AO system is used to evaluate and then reduce the aberrations in the at least correcting path; (2) control signals towards the wavefront corrector 22 are memorised, (3) the link between the wavefront sensor 23 and the wavefront corrector 22 is interrupted and (4) T-scan are performed, while the same correction of aberrations according to the stored values in step 2 is maintained. The signals provided to corrector 22 can be combined with controlling signal to change the focus of the object beam, as described in connection with the embodiments in FIG. 1 and FIG. 3. These focus adjusting signals are applied to the wavefront corrector, to modify the position in depth where both channels, confocal and OCT focus and T-scans are collected from.

Single Path Correction, Closed Loop

If mirrors are used in the interface optics 7 in FIG. 5, the group of beamsplitter 76 and source 21 could be placed anywhere along the common and uncommon OCT and confocal paths. If the group is placed before scanners 61 and 62, it allows aberration compensation at any tilt of the scanners 61 and 62 and not only along single axis.

Selection Between Single Path and Dual Path Correction, Via Mirrors

If mirrors are used in the interface optics 7 in FIG. 5, then source 11 could also serve as providing the wavefront sensing beam. A band pass filter 236 could be chosen to select either the wavelength of the source 11 or that of the source 21. To allow for good spectral selection, the wavelengths should be sufficient distant apart. For instance, 11 could be a low coherent source operating at 820 nm and 21 a laser or another low coherent source operating at 750 nm. When selecting the wavelength of the source 21 using the filter 236, the correction is single path. When selecting the wavelength of the source 11, the correction is either single path or double path, depending on the focal length of the focusing element 110. If a short focal length element is used, then the correction is single path too, if a long focal element is used, then the correction is dual path. Such a selection allows such an embodiment to correct aberrations either: 1. in dual path for the OCT and confocal channels or in single path for the fluorescence channel only; 2 in single path for all channel, OCT, confocal and fluorescence. Such a versatile system could be used in research to evaluate how important is for the fluorescence generation the enhanced concentration of radiation which takes place when dual correction is used.

Aberrations Free Fluorescence Channel Using Lenses, Open Loop

The same comments in terms of best choice of neutral beamsplitters or dichroic beamsplitters are valid as mentioned during the presentation of the embodiment in FIG. 1, in order to minimise the losses in the 3 channels. However, by using a different source 21 for the wavefront sensor 22, as shown in FIG. 5, a dual system OCT/fluorescence channel could be implemented using lenses instead of mirrors in the interface optics, i.e. elements of interface optics 51 to 54 and 71 to 74 could be lenses, as the reflection of the beam from source 11 does not upset the photodetector 235 in the wavefront sensor 23, if the wavefront sensor beam is from source 21, preferably chosen close to the fluorescence band. Such an embodiment could operate in open loop only, according to the following steps: (1) with no depth scanning and no T-scanning, i.e. with the scanners 61 and 62 fixed on tilts to direct the object beam along the direction of the wavefront sensing beam, the AO system is used to evaluate and then reduce the aberrations in the at least correcting path; (2) control signals towards the wavefront corrector 22 are stored, (3) the link between the wavefront sensor 23 and the wavefront corrector 22 is interrupted and (4) source 21 is switched off and T-scan are performed, while the same correction of aberrations according to the stored values in step 2 is maintained. The signals provided to corrector 22 can be combined with controlling signal to change the focus of the object beam, as described in connection with the embodiment in FIG. 1 to produce B-scans and C-scans in the OCT and the fluorescence channel. If a large beam diameter is launched by source 11, then the OCT and confocal channels are not corrected for aberrations while the fluorescence channel only is.

Focus adjusting signals can be applied to the wavefront corrector 22, to modify the position in depth where the three channels, fluorescence, confocal and OCT focus and T-scans are collected from. However, if aberrations are not corrected in the OCT and confocal channels, depth resolved B-scans and C-scans are obtained in the OCT and fluorescence channel.

The system could operate as a 3 imaging channel system, OCT, confocal on the same wavelength as that of the OCT channel and fluorescence channel, as described in the presentation of the embodiment of FIG. 1, either sequential confocal/fluorescence by shifting the spectral filter 124 or simultaneous confocal/fluorescence by using a dichroic beamsplitter to separate after beamsplitter 32, the wavelength of source 11 for the confocal channel and the fluorescence signal for the fluorescence channel. The confocal aperture 123 in the confocal channel is sufficient to eliminate or reduce reflections from the interface elements 51, 52, 71 and 72, and from the focusing elements 53, 54, if they are lenses.

Figure 6:
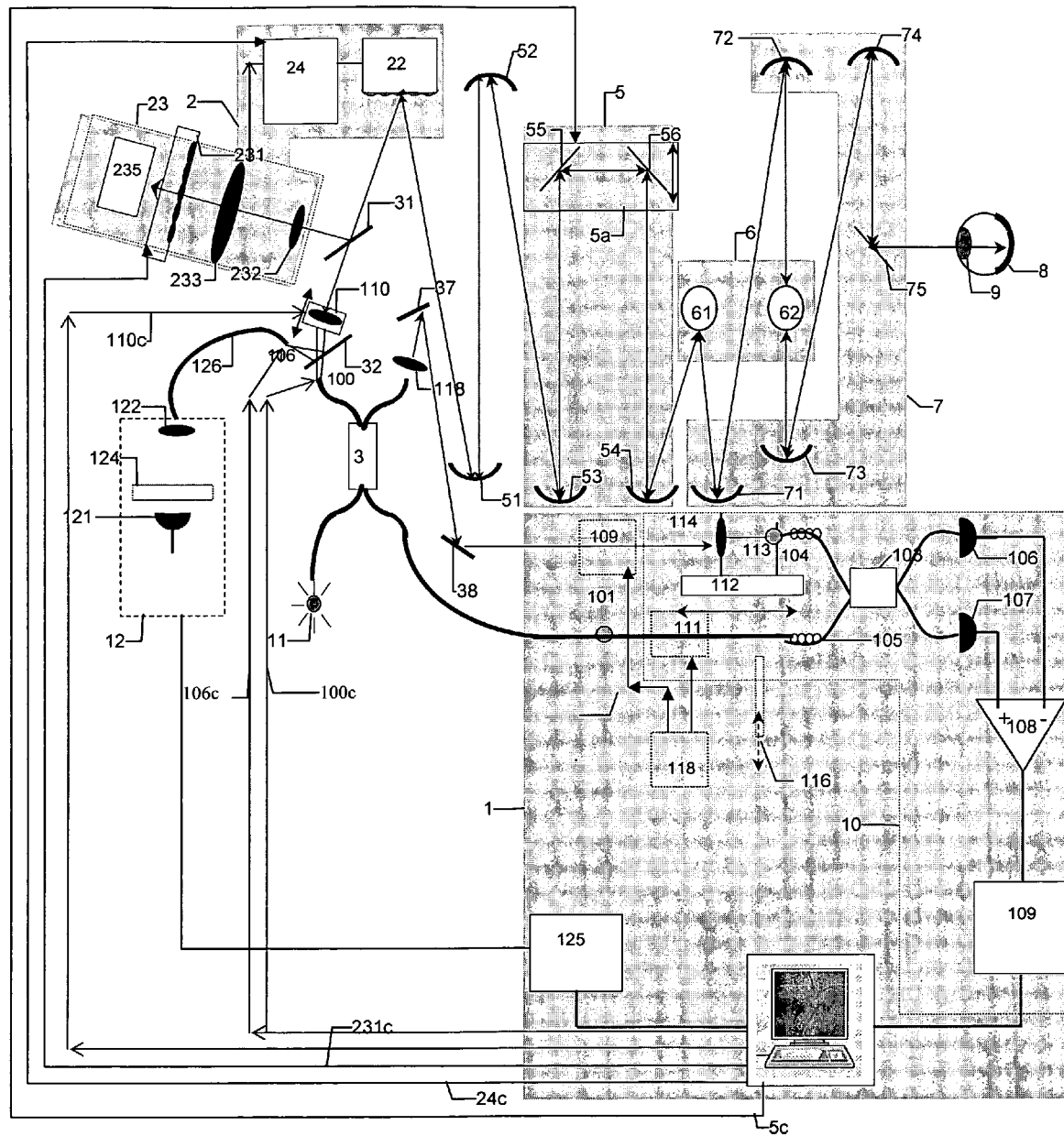
FIG. 6 shows a fifth embodiment of the system for high resolution imaging of an object via an aberrated path.

FIG. 6 shows a fifth embodiment of the system for high resolution imaging, where a common focus element 110 is used for both OCT and confocal channels in the uncommon path. The OCT splitter 3 is in single mode fibre and tied by fibre to transfer light from the object 8 to the input 101 of the balanced splitter 103. The aperture of the confocal receiver at the core of the OCT is now at the fibre tip 106 of the fibre 126, behind the splitter 32. Light diverges out from the aperture fibre. 100. By axially moving the collimating element 110, the convergence of the beam sent to the interface optics 7 changes. The aperture of the OCT input, 100, is conjugate by virtue of beamsplitter 32 with the confocal aperture 106, here implemented in fibre 126, which could be single mode or multimode. Input 110 could be moved under computer, e,g, PC 4 control, showed by control line 110c. Irrespective of focus correction by elements 55 and 56, or the deformation of the corrector 22, the two fibre apertures 100 and 106 are all the time conjugated. These could be moved away from the conjugate initial points, in case separate depth adjustments are required in the two channels, in which case similar functionality is achieved as described in the focus procedures presented in connection to the embodiment in FIG. 1. Control lines could equally be applied to the two fibre tips, 100 and 103, as shown by 100c and 106c.

The reference beam exists the splitter 3 and is collimated via focusing element 18 and rerouted via mirrors 37 and 38 (optional) towards the reference input of the balanced splitter 103.

The combination of input 110 and apertures 100 and 106 is maximised for maximum signal collected in the splitter 3. The beam diameter captured into the fibre is the same with the beam diameter generated by the output beam from 100, therefore such a configuration can only be used for dual path correction. (Single path correction as discussed in connection with FIGS. 1 and 5 requires different beam diameters of the incident and emergent beams).

Due to fiber end reflection in 100, this configuration cannot be used for sequential OCT/confocal operation, only for simultaneous regime using a separate confocal receiver 12 as shown in FIG. 5.

However, the embodiment in FIG. 6 has the advantage of using a compact interferometer, in fibre and focusing via a lens or microscope objective 110 in the uncommon 2-path, which can eliminate the need for the focusing element 5 in the path to the object. A single element 110 could now be moved to keep both confocal and OCT apertures in focus. Preferably, to keep the dispersion low, the splitter 32 is used in reflection by the OCT and in transmission by the confocal channel.

Figure 7:
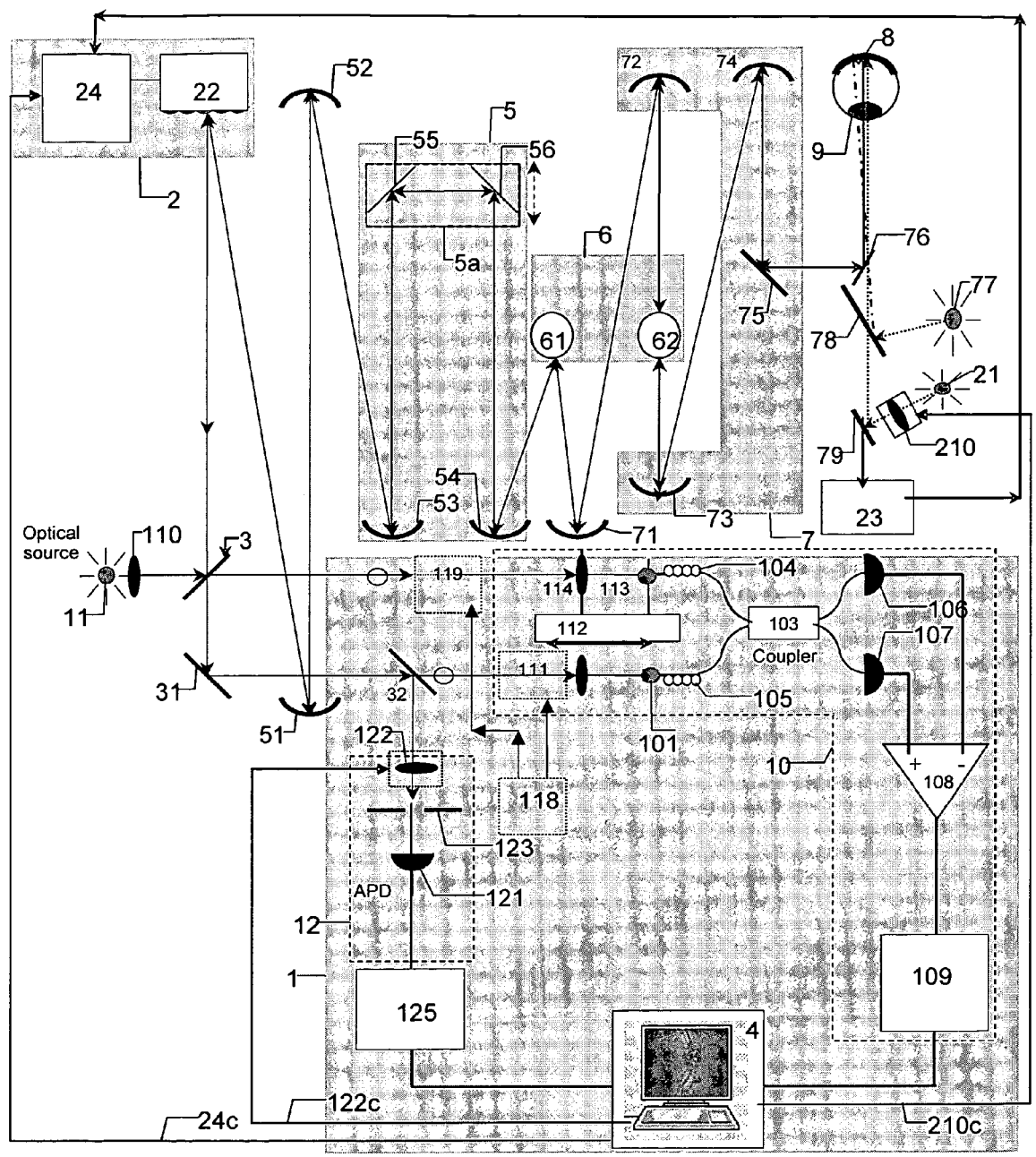
FIG. 7 shows a sixth embodiment of the system for high resolution imaging of an object via an aberrated path.

FIG. 7 shows another embodiment of the system for high resolution imaging that is generally similar to FIG. 1, where the wavefront sensing beam is sent towards the object 8, via a fixation lamp filter, 76 and the wavefront sensor 22 does not sense the effect of the corrector. This is a dichroic filter or a hot mirror, which reflects the light from the source 11, in case of the eye, 800 nm. This also allows light from fixation lamp, 77 to be transferred towards the eye 9, preferably yellow or green. By moving spatially the optical source 77, the eye is guided and such an operation is known for those in the art of eye imaging. A low reflectivity splitter, 78 is used to send light from the fixation lamp 77 to the eye. For maximum transmittance of the light reflected from the object, 8, towards the wavefront sensor 23, preferably splitters 78 and 79 have a high transmittance. The fixation filter 76 is incorporated within the interface optics, by means known in the art. Equally, it could be placed between mirrors 73 and 74 with matched convergence to the common path beam. In this embodiment, the confocal receiver and the OCT use a different wavelength to that of the AO channel. The source 21 could be a low coherence source or a laser while source 11 is a low coherence source. This embodiment may have the disadvantage of different optical path for the AO and the imaging system OCT and confocal, which may lead to noncompensation of aberrations in the OCT and confocal channel due to interface optics and scanning. However, as long as the main distortions are due to the object, this may not be too disadvantageous. The common path reduces in this embodiment to the path from splitter 76 to the object 8.

In the embodiment in FIG. 7, it is considered that the main aberrations are due to the object and the scanning and interface optics do not add any wavefront distortions. While the corrector 22 in FIG. 7 is used to compensate for the object aberrations, it is also possible to include a second corrector in series with a different time constant, to correct for the internal system aberrations. This will require another wavefront sensor, possible like in the embodiments in FIGS. 1, 3 or 4. Such an embodiment will have two correctors, 22, in series, one external, under the control of the wavefront sensor 23 in the fixation lamp, as shown in FIG. 7 and the other one internal, under the control of the wavefront sensor in FIG. 1. The two correctors could be sensitive to two different types of signal. The internal corrector is trained using a non-aberrated object and corrections are stored depending on the inclination of the scanning beam. Then, in the process of scanning an object, the internal corrector is driven by the stored values of control signals while the external corrector is under the real time control of the wavefront sensor in the fixation lamp. In this way, aberrations due to scanning and aberrations due to the object are compensated for. The correctors could be customised for these two different tasks, for example, one corrector with the main task of compensating for scanning corrections, for large defocus aberrations, using a smaller number of actuators, and the other for higher aberrations due to the object, which requires a large number of actuators.

In figures above mirrors are used for the focus and interface optics, however lenses could equally be used if antireflection layers are optimally used to avoid stray reflections and chromatic elements to accommodate the large band of the OCT source 11 and the large spread of frequencies when using different wavelengths for OCT, confocal receiver, fluorescence and wavefront correction.

It will be apparent that the above mentioned improvements in focussing using the wavefront corrector 23 and the wavefront sensor 22 could equally be applied to arrangements that combine a OCT system and an AO system, without a confocal system present. Such embodiments could produce a T-scan, a C-scan or a B-scan as described above.

Similarly, the above mentioned improvements in focussing using the wavefront corrector 23 and the wavefront sensor 22 could equally be applied to arrangements that combine a confocal system and an AO system, without an OCT system present. Such embodiments could produce a T-scan, a C-scan or a B-scan as described above.

What is claimed is:

1. Optical mapping apparatus for imaging an object, comprising:
   an optical coherence tomography (OCT) system including:
      an OCT source,
      an OCT reference path leading from the OCT source to an OCT receiver, an OCT object path leading from the object to the OCT receiver, and
      an OCT depth scanner adapted to alter at least one of the OCT reference path and the OCT object path so as to adjust an OCT optical path difference to enable the OCT system to obtain OCT image data from different axial depths within the object;
   a confocal system including:
      a confocal source,
      a confocal optical receiver, and
      a confocal path leading from the object to the confocal optical receiver, the confocal system being arranged to obtain confocal image data from the object;
   an adaptive optics (AO) system including:
      a wavefront corrector and a wavefront sensor,
      the adaptive optics system being arranged to transfer a wavefront sensing beam along a wavefront sensing path leading from the object to the wavefront sensor, and;
      wherein the apparatus is arranged such that there is a first common path shared by a portion of the wavefront sensing path, a portion of the OCT object path and a portion of the confocal path, and there is a second common path shared by a portion of the OCT object path and a portion of the confocal path, and
   wherein the adaptive optics system is adapted to correct for optical aberrations in the first common path by means of the actuation of the wavefront corrector under control of the wavefront sensor.

2. Optical mapping apparatus according to claim 1, further comprising:
   a scanner located in the second common path for scanning an optical beam from at least one of the OCT source and the confocal source over a predetermined area;
   interface optics for transferring an optical beam from said scanner to the object and for transferring an optical output beam reflected and scattered from the object back along said second common path through said scanning means.

3. Optical mapping apparatus according to claim 2, wherein the scanner comprises a line scanner and a frame scanner.

4. Optical mapping apparatus according to claim 3, wherein the scanner is arranged so as to enable the apparatus to produce T-scans of the object for at least one of the OCT system and confocal system.

5. Optical mapping apparatus according to claim 4, wherein the apparatus is arranged to produce C-scans for at least one of the OCT system and confocal system by combining a number of different T-scans from a predetermined depth in the object.

6. Optical mapping apparatus according to claim 4, wherein the apparatus is arranged to produce B-scans for at least one of the OCT system and confocal system by combining a number of different T-scans from different axial depths in the object.

7. Optical mapping apparatus according to claim 6, wherein start depth and end depth for generating the B-scans for the OCT system and the confocal system are independently controlled.

8. Optical mapping apparatus according to claim 1, wherein first focussing means is provided in the second common path, the first focussing means being arranged to focus light from the OCT source and/or the confocal source at different axial depths within the object for imaging.

9. Optical mapping apparatus according to claim 8, wherein the first focussing means is arranged to adjust the focus synchronously with the use of the OCT depth scanner to adjust the OCT optical path difference.

10. Optical mapping apparatus according to claim 8, wherein the first focussing means comprises the wavefront corrector.

11. Optical mapping apparatus according to claim 8, wherein the first focussing means is in a portion of the second common path that is not shared with the first common path.

12. Optical mapping apparatus according to claim 8, wherein the wavefront sensor comprises a wavefront sensor focussing element and a photodetector array, the wavefront sensor focussing element being arranged to adjust the focus of light transferred onto the wavefront sensor so as to select different axial depths within the object for imaging.

13. Optical mapping apparatus according to claim 12, wherein the wavefront sensor focussing element comprises an axially moveable lenslet array.

14. Optical mapping apparatus according to claim 12, wherein the wavefront sensor focussing element comprises a lenslet array with an electronically variable focal length.

15. Optical mapping apparatus according to claim 1, wherein the apparatus comprises an OCT/confocal splitter arranged to split light from the object transferred via the second common path into an uncommon OCT path that is portion of the OCT path that is not common with the confocal path and into an uncommon confocal path that is not common with the OCT path.

16. Optical mapping apparatus according to claim 15, wherein a second focussing element is provided in the uncommon confocal path, the second focussing element being arranged to focus light from the confocal source that has been reflected from the object at different axial depths within the object for confocal imaging.

17. Optical mapping apparatus according to claim 16, wherein the second focussing element is arranged to adjust the focus synchronously with using the OCT depth scanner to adjust the OCT optical path difference.

18. Optical mapping apparatus according to claim 16, wherein the second focussing element is adapted to enable independent control of the axial depth within the object from which the OCT image data is obtained and the axial depth within the object from which the confocal image data is obtained.

19. Optical mapping apparatus according to claim 1, wherein a third focussing element is provided in the uncommon OCT path, the third focussing element being arranged to focus light from the OCT source that has been reflected from the object at different axial depths within the object for OCT imaging.

20. Optical mapping apparatus according to claim 19, wherein the third focussing element is arranged to adjust the focus synchronously with using the OCT depth scanner to adjust the OCT optical path difference.

21. Optical mapping apparatus according to claim 19, wherein the third focussing element is adapted to enable independent control of the axial depth within the object from which the OCT image data is obtained and the axial depth within the object from which the confocal image data is obtained.

22. Optical mapping apparatus according to claim 1, wherein the apparatus comprises an OCT display for generating and processing an image from the image data obtained by the OCT system.

23. Optical mapping apparatus according to claim 22, wherein the image generated by the OCT display is a T-scan, a C-scan or a B-scan.

24. Optical mapping apparatus according to claim 1, wherein the apparatus comprises a confocal display for generating and processing an image from the image data obtained by the confocal system.

25. Optical mapping apparatus according to claim 24, wherein the image created by the confocal system is a T-scan, a C-scan or a B-scan.

26. Optical mapping apparatus according to claim 1, wherein the apparatus comprises an OCT display for generating and processing an OCT image from the image data obtained by the OCT system and a confocal display for generating and processing a confocal image from the image data obtained by the confocal system.

27. Optical mapping apparatus according to claim 26 wherein the OCT image and the confocal image are both a T-scan, a C-scan or a B-scan.

28. Optical mapping apparatus according to claim 26, wherein the apparatus is arranged to simultaneously display the OCT image and the confocal image.

29. Optical mapping apparatus according to claim 1, wherein the OCT source is the same optical source as the confocal source.

30. Optical mapping apparatus according to claim 1, wherein the wavefront sensing path is arranged to lead from the object to the wavefront sensor via the corrector.

31. Optical mapping apparatus according to claim 1, wherein the apparatus further comprising a wavefront sensing source, the apparatus being arranged such that a wavefront sensing beam from the wavefront sensing source is transferred to the object and back from the object via the wavefront sensing path.

32. Optical mapping apparatus according to claim 31, wherein the wavefront sensing source is not the same source as either the OCT source or the confocal source.

33. Optical mapping apparatus according to claim 31, wherein a wavefront sensor source focussing element is provided in a path between the wavefront sensor source and the object, wavefront sensor source focussing element being arranged to adjust the focus of light transferred onto the wavefront sensor so as to select different axial depths within the object.

34. Optical mapping apparatus according to claim 1, wherein the wavefront sensing path is arranged to lead from the object to the wavefront sensor not via the corrector.

35. Optical mapping apparatus according to claim 1, wherein a beam from the OCT source or the confocal source is transferred to the object and reflected so as to form the wavefront sensing beam.

36. Optical mapping apparatus according to claim 1, wherein the first common path and the second common path are shared paths up to a wavefront sensing splitter.

37. Optical mapping apparatus according to claim 1, wherein the confocal receiver is the same optical receiver as the OCT receiver.

38. Optical mapping apparatus according to claim 37, wherein the apparatus comprises a blocking member adapted to block light in the OCT reference path from reaching the shared confocal and OCT receiver so as to enable the confocal receiver to obtain confocal image data.

39. Optical mapping apparatus for imaging an object, comprising:
an optical coherence tomography (OCT) system including:
an OCT source,
an OCT reference path leading from the OCT source to an OCT receiver, an OCT object path leading from the object to the OCT receiver, and
an OCT depth scanner adapted to alter at least one of the OCT reference path and the OCT object path so as to adjust an OCT optical path difference to enable the OCT system to obtain OCT image data from different axial depths within the object;
an adaptive optics (AO) system including:
a wavefront corrector and a wavefront sensor,
the adaptive optics system being arranged to transfer a wavefront sensing beam along a wavefront sensing path leading from the object to the wavefront sensor, and;
wherein the apparatus is arranged such that there is a first common path shared by a portion of the wavefront sensing path, and a portion of the OCT object path, and
wherein the adaptive optics system is adapted to correct for optical aberrations in the first common path by means of the actuation of the wavefront corrector under control of the wavefront sensor, the apparatus further comprising:
a first focussing means provided in the first common path, the first focussing means being arranged to focus light from the OCT source at different axial depths within the object for imaging, wherein the first focussing means comprises the wavefront corrector.

40. Optical mapping apparatus according to claim 39, wherein the first focussing means is arranged to adjust the focus synchronously with the use of the OCT depth scanner to adjust the OCT optical path difference.

41. Optical mapping apparatus according to claim 39, wherein the wavefront sensor comprises a wavefront sensor focussing element and a photodetector array, the wavefront sensor focussing element being arranged to adjust the focus of light transferred onto the wavefront sensor so as to select different axial depths within the object for imaging.

42. Optical mapping apparatus according to claim 41, wherein the wavefront sensor focussing element comprises an axially moveable lenslet array.

43. Optical mapping apparatus according to claim 41, wherein the wavefront sensor focussing element comprises a lenslet array with an electronically variable focal length.

44. Optical mapping apparatus according to claim 39, wherein the apparatus further comprising a wavefront sensing source, the apparatus being arranged such that a wavefront sensing beam from the wavefront sensing source is transferred to the object and back from the object via the wavefront sensing path.

45. Optical mapping apparatus according to claim 44, wherein the wavefront sensing source is not the same source as the OCT source.

46. Optical mapping apparatus according to claim 44, wherein a wavefront sensor source focussing element is provided in a path between the wavefront sensor source and the object, wavefront sensor source focussing element being arranged to adjust the focus of light transferred onto the wavefront sensor so as to select different axial depths within the object.

47. Optical mapping apparatus according to claim 39, wherein the image data generated by the OCT system can be used to generate a T-scan, a C-scan or a B-scan.

* * * * *